(12) United States Patent
Regan et al.

(10) Patent No.: US 9,217,175 B2
(45) Date of Patent: Dec. 22, 2015

(54) MULTIPLEXED DIGITAL ASSAY WITH SPECIFIC AND GENERIC REPORTERS

(71) Applicant: Bio-Rad Laboratories, Inc., Hercules, CA (US)

(72) Inventors: John F. Regan, San Mateo, CA (US); Svilen S. Tzonev, Pleasanton, CA (US); Yann Jouvenot, Benicia, CA (US); Claudia Litterst, Walnut Creek, CA (US); Dianna Maar, Mountain House, CA (US); Geoff McDermott, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 47 days.

(21) Appl. No.: 14/171,761

(22) Filed: Feb. 3, 2014

(65) Prior Publication Data

US 2014/0221238 A1      Aug. 7, 2014

Related U.S. Application Data

(60) Provisional application No. 61/759,772, filed on Feb. 1, 2013, provisional application No. 61/759,930, filed on Feb. 1, 2013, provisional application No. 61/759,931, filed on Feb. 1, 2013.

(51) Int. Cl.
*C12Q 1/68* (2006.01)
*C07H 21/02* (2006.01)
*C07H 21/04* (2006.01)

(52) U.S. Cl.
CPC .................................. *C12Q 1/6851* (2013.01)

(58) Field of Classification Search
CPC ........... C12Q 1/6851; C12Q 2537/143; C12Q 2537/165; C12Q 2545/107
See application file for complete search history.

(56) References Cited

U.S. PATENT DOCUMENTS

| 8,148,515 | B1 | 4/2012 | Mao et al. |
| 2011/0104686 | A1 | 5/2011 | Litterst et al. |
| 2011/0250597 | A1* | 10/2011 | Larson et al. ................ 435/6.11 |
| 2012/0164690 | A1 | 6/2012 | Wang |
| 2012/0322058 | A1 | 12/2012 | Regan et al. |

FOREIGN PATENT DOCUMENTS

WO    WO 2011/143478    * 11/2011

OTHER PUBLICATIONS

Lind, K. et al., Biotechniques, vol. 40, pp. 315-318 (2006).*
Manit Arya et al., "Basic principles of real-time quantitative PCR", Expert Rev. Mol. Diagn., Mar. 2005, vol. 5, No. 2, pp. 209-219.

(Continued)

*Primary Examiner* — Teresa E Strzelecka
(74) *Attorney, Agent, or Firm* — Kolisch Hartwell, P.C.

(57) ABSTRACT

Digital assay system, including methods, apparatus, and compositions, for performing target assays in partitions each containing a generic reporter and a specific reporter for target amplification.

20 Claims, 17 Drawing Sheets

(56) References Cited

OTHER PUBLICATIONS

Geoffrey P. McDermott et al., "Multiplexed Target Detection Using DNA-Binding Dye Chemistry in Droplet Digital PCR", Anal. Chem., Nov. 3, 2013, vol. 85, pp. 11619-11627.
Lee W. Young, Authorized Officer, International Searching Authority, U.S. Patent and Trademark Office, "International Search Report" in connection with related PCT Patent Application No. PCT/US2014/014515, dated May 13, 2014, 2 pages.
Lee W. Young, Authorized Officer, International Searching Authority, U.S. Patent and Trademark Office, "Written Opinion of the International Searching Authority" in connection with related PCT Patent Application No. PCT/US2014/014515, dated May 13, 2014, 6 pages.

\* cited by examiner

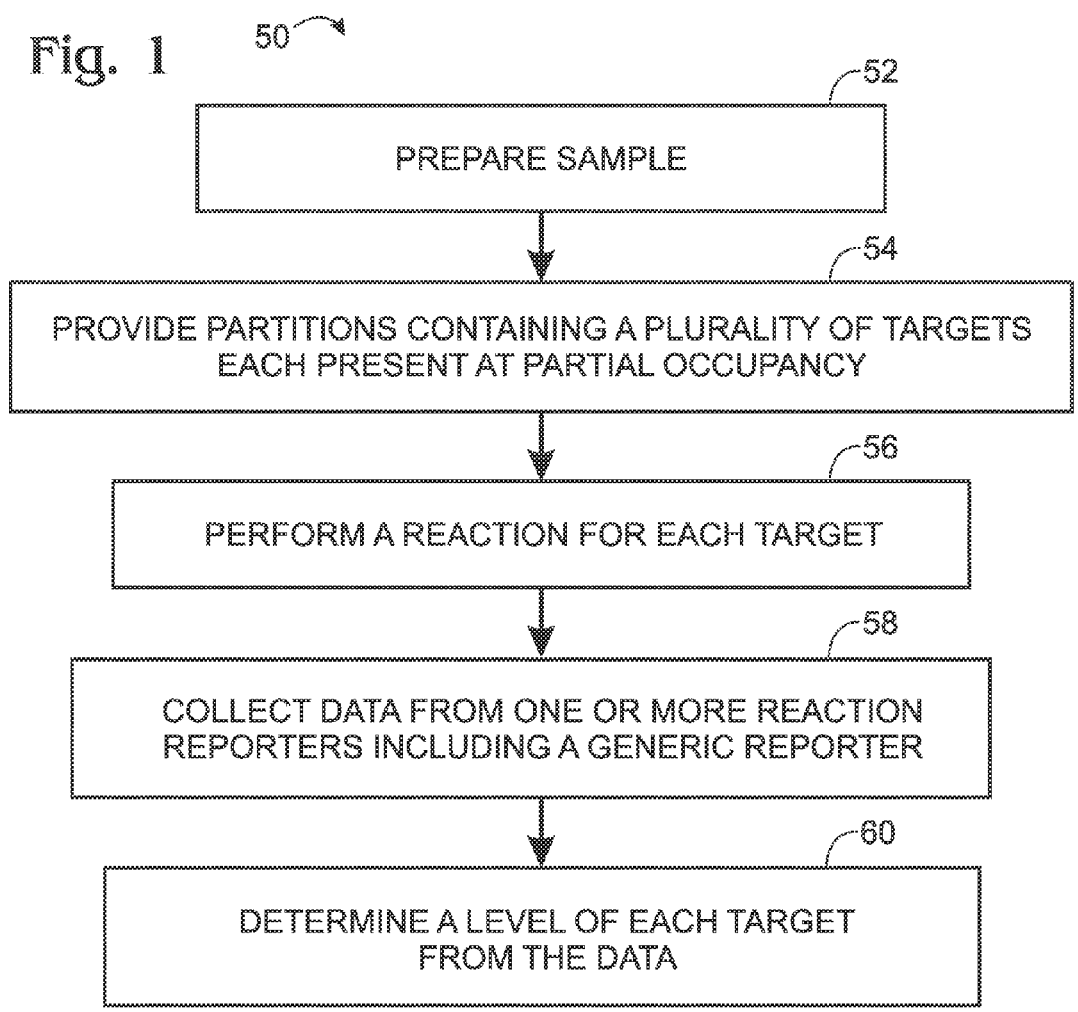
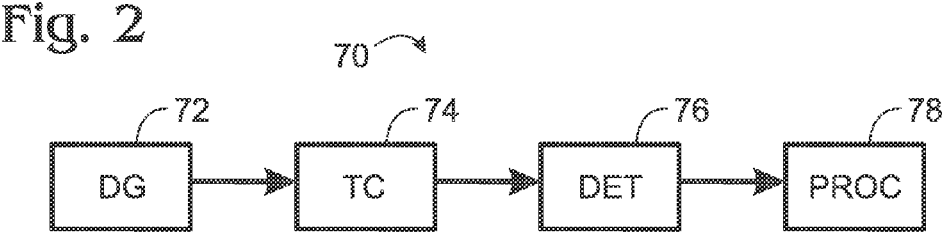

Fig. 14A
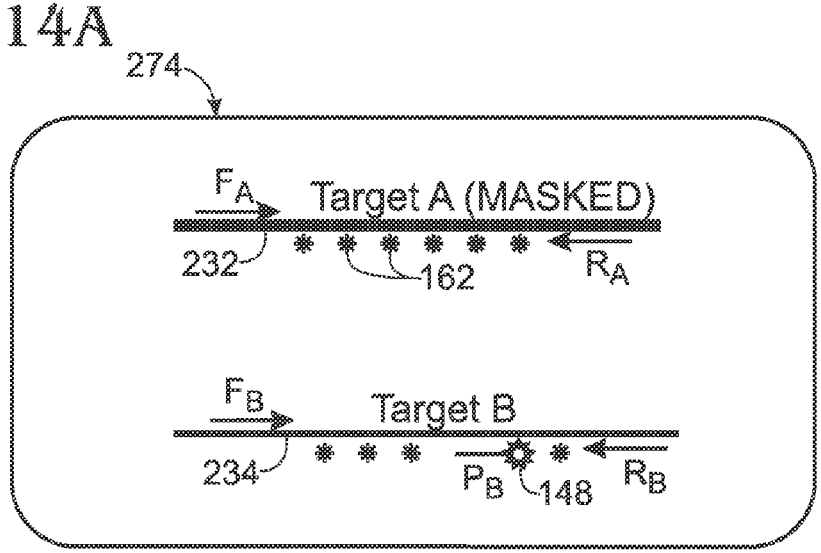
Fig. 14B
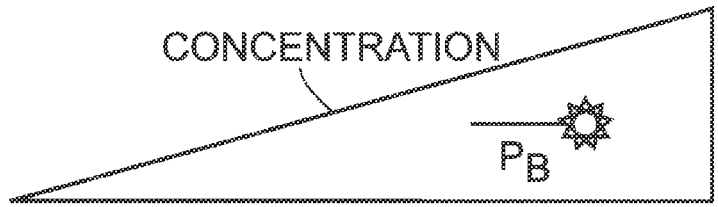
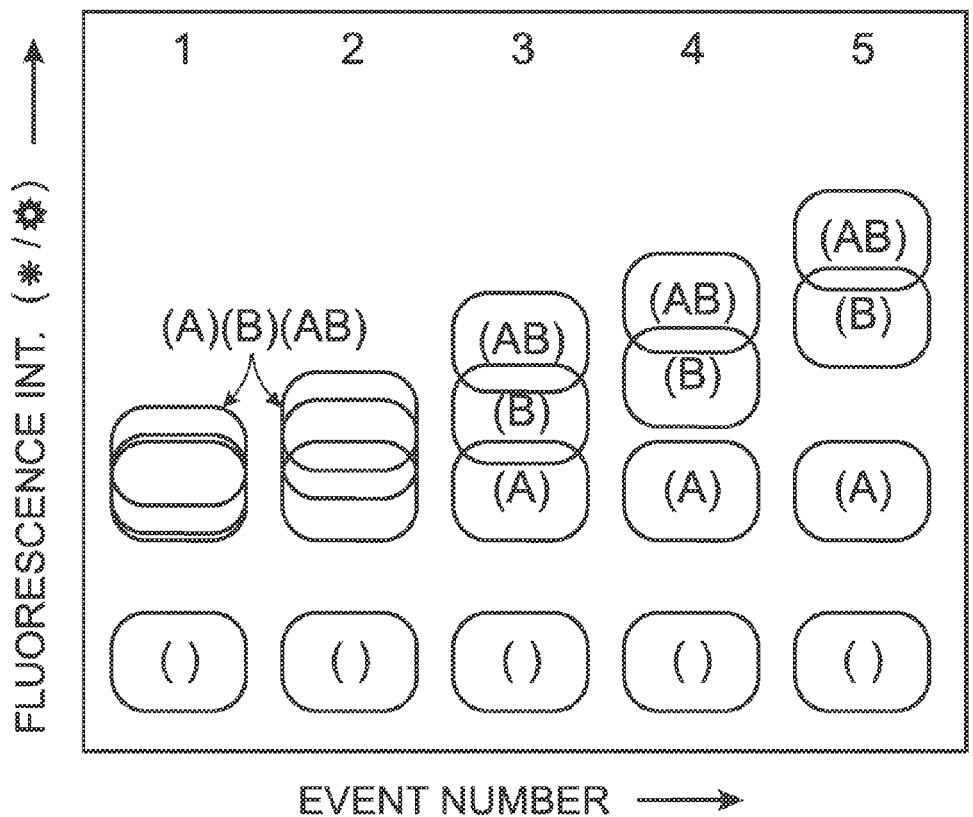

MULTIPLEXED DIGITAL ASSAY WITH SPECIFIC AND GENERIC REPORTERS

CROSS-REFERENCES TO PRIORITY APPLICATIONS

This application is based upon and claims the benefit under 35 U.S.C. §119(e) of U.S. Provisional Patent Application Ser. No. 61/759,772, filed Feb. 1, 2013; U.S. Provisional Patent Application Ser. No. 61/759,930, filed Feb. 1, 2013; and U.S. Provisional Patent Application Ser. No. 61/759,931, filed Feb. 1, 2013. Each of these priority applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. Patent Application Publication No. 2013/0040841 A1, published Feb. 14, 2013; U.S. patent application Ser. No. 14/099,750, filed Dec. 6, 2013; and Joseph R. Lakowicz, PRINCIPLES OF FLUORESCENCE SPECTROSCOPY ($2^{nd}$ Ed. 1999).

INTRODUCTION

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or the negative fraction then may be utilized to determine the concentration of the analyte in the partitions, such as with Poisson statistics.

Digital assays frequently rely on amplification of a nucleic acid target in partitions to enable detection of a single copy of an analyte. Amplification may be conducted via the polymerase chain reaction (PCR), to achieve a digital PCR assay. The target amplified may be the analyte itself or a surrogate for the analyte generated before or after formation of the partitions. Amplification of the target can be detected optically from a fluorescent probe included in the reaction. In particular, the probe can include a fluorophore that provides a fluorescence signal indicating whether or not the target has been amplified.

A digital PCR assay can be multiplexed to permit detection of two or more different targets within each partition. Amplification of the targets can be distinguished by utilizing target-specific probes. However, such probes can be expensive and need to be custom-synthesized, if not already available commercially, further increasing the cost.

New approaches are needed for performing multiplexed digital assays of more targets with fewer target-specific probes.

SUMMARY

The present disclosure provides a digital assay system, including methods, apparatus, and compositions, for performing target assays in partitions each containing a generic reporter and a specific reporter for target amplification.

BRIEF DESCRIPTION OF THE DRAWINGS

FIG. 1 is a flowchart of an exemplary method of performing a multiplexed digital assay on targets in partitions containing a generic reporter, optionally with at least one of the targets being an obscuring target that at least partially masks the presence of another target in partitions containing both the obscuring target and the masked target, in accordance with aspects of the present disclosure.

FIG. 2 is a schematic view of an exemplary system for performing the multiplexed digital assay of FIG. 1, in accordance with aspects of the present disclosure.

FIG. 14A is a schematic view of a partition from an exemplary multiplexed digital assay performed with a single detection channel, with the partition containing a copy of a masked target (A) and a copy of a masking target (B), each amplifiable with a different pair of forward and reverse primers ($F_A$ and $R_A$ or $F_B$ and $R_B$) and detectable via a generic reporter (e.g., an intercalating dye) and a specific probe ($P_B$), in accordance with aspects of the present disclosure.

FIG. 14B is a schematic graph of fluorescence intensity data that may be collected from five sets of partitions (lanes 1-5) in a single detection channel for the multiplexed digital assay of FIG. 14A, with each set containing the same concentrations of targets A and B and of both pairs of primers, and a variable concentration of the probe ($P_B$) for target B, in accordance with aspects of the present disclosure.

DETAILED DESCRIPTION

Figure 3:
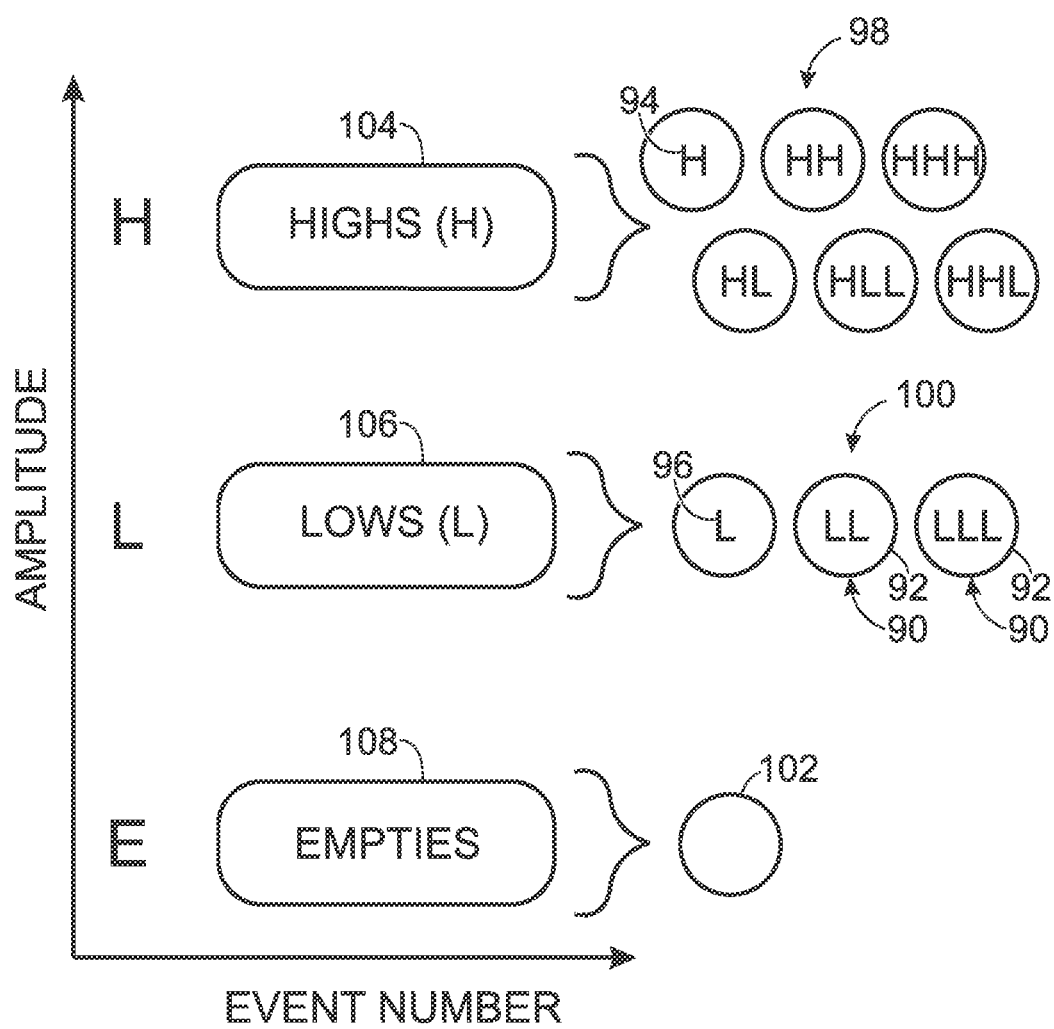
FIG. 3 is a schematic graph of multiplexed assay data that may be collected in a single detection channel from partitions, such as droplets, collectively containing an obscuring target (H) associated with a higher amplitude signal and a masked target (L) associated with a lower amplitude signal, in accordance with aspects of the present disclosure.

The present disclosure provides a digital assay system, including methods, apparatus, and compositions, for performing target assays in partitions each containing a generic reporter and a specific reporter for target amplification.

A method of performing a multiplexed digital assay is provided. In the method, partitions may be provided, with each partition including a portion of a same mixture. The mixture may contain a first target and a second target and also may contain a generic reporter that is sensitive to amplification of either target and a specific reporter that is specifically sensitive to amplification of the second target. Only a first subset of the partitions each may contain at least one copy of the first target and only a distinct second subset of the partitions each may contain at least one copy of the second target. The first target and the second target may be amplified in the partitions. Amplification data may be collected from the generic reporter and the specific reporter present in a plurality of the partitions. A level of each target may be calculated based on the amplification data.

Another method of performing a multiplexed digital assay is provided. In the method, partitions each including a portion of a same mixture may be provided, with the mixture containing a first target and a second target and also containing a generic reporter and a specific reporter. Only a subset of the partitions each may contain at least one copy of the first target and only another subset of the partitions each may contain at least one copy of the second target. The targets may be amplified in the partitions to generate a first amplicon corresponding to the first target and a second amplicon corresponding to the second target. The generic reporter may bind to the first amplicon and the second amplicon. The specific reporter may bind to the second amplicon and not the first amplicon. Amplification data may be collected from a plurality of the partitions by detecting light emitted by the generic reporter and at least one luminophore of the specific reporter. A level of each target may be calculated based on the amplification data.

A composition for performing a multiplexed digital assay is provided. The composition may comprise a plurality of droplets disposed in a same continuous phase. The droplets each may include a portion of a same mixture. The mixture may contain a first target, a second target, a generic reporter that is sensitive to amplification of either target, and a specific reporter that is specifically sensitive to amplification of the second target. Only a first subset of the plurality of droplets each contain at least one copy of the first target and only a distinct second subset of the plurality of droplets each contain at least one copy of the second target. The mixture may include a complete set of reagents for amplification of each target.

The digital assays of the present disclosure may have numerous advantages, such as higher levels of multiplexing, multiplexing with a generic reporter alone or in combination with at least one specific reporter, determination of target levels (e.g., concentrations) with partition populations that are indistinguishable and/or not well resolved in the data, determination of target levels using competing assays within partitions, or any combination thereof, among others.

Further aspects of the present disclosure are presented in the following sections: (I) overview of multiplexed digital assays with a generic reporter, (II) determination of concentration for masked targets, (III) exemplary assay configurations with target masking, (IV) multiplexed assays with a specific reporter and a generic reporter, and (V) examples.

I. OVERVIEW OF MULTIPLEXED DIGITAL ASSAYS WITH A GENERIC REPORTER

This section provides an overview of multiplexed digital assays performed with a generic reporter and, optionally, in which the presence of a target in a partition is at least partially masked by the presence of a different target in the same partition; see FIGS. 1 and 2. The digital assays may utilize data exclusion as described Section II and elsewhere herein to calculate a level of one or more of the targets.

FIG. 1 shows a flowchart of an exemplary method 50 of performing a multiplexed digital assay with a generic reporter, optionally with target masking. The steps presented for method 50 may be performed in any suitable order and in any suitable combination. Furthermore, the steps may be combined with and/or modified by any other suitable steps, aspects, and/features of the present disclosure, including those described in the patent documents listed above under Cross-References, which are incorporated herein by reference.

Sample Preparation.

A sample may be prepared for the assay, indicated at 52. Preparation of the sample may include any suitable manipulation of the sample, such as collection, dilution, concentration, purification, lyophilization, freezing, extraction, combination with one or more assay reagents to form a mixture (also termed a sample-containing mixture, a bulk phase, or a reaction mixture), performance of at least one preliminary reaction to prepare the sample for one or more reactions in the assay, or any combination thereof, among others. The preparation may isolate an analyte, such as nucleic acid that includes copies of one or more nucleic acid targets, and/or may modify and/or fragment the analyte. Preparation of the sample may include rendering the sample competent for subsequent performance of one or more reactions, such as one or more enzyme catalyzed reactions and/or binding reactions.

In some embodiments, preparation of the sample may include combining the sample with reagents to produce a sample-containing mixture for performing a reaction (such as an amplification reaction) for each target and for reporting an extent of each reaction (e.g., whether or not the reaction occurred above a threshold level or within a range). Reagents for amplification may include any combination of primers for targets, dNTPs and/or NTPs, at least one enzyme (e.g., a polymerase, a ligase, a reverse transcriptase, a restriction enzyme, or a combination thereof, among others, each of which may or may not be heat-stable), and/or the like. Accordingly, the mixture may have a complete set of reagents for (i.e., may be competent for) amplification of each target under suitable environmental conditions (e.g., incubation at an elevated temperature or modulation of temperature (such as by thermocycling)). The mixture may be capable of amplification of each of one or more targets, if present, in the sample (or a partition thereof). Reagents for reporting may include at least one generic reporter and/or at least one specific reporter. The generic reporter may be sensitive to amplification of each target and the specific reporter may be specifically sensitive to amplification of only a subset of the targets, such as only one of the targets. The mixture may or may not include a different reporter for each target to be assayed. Preparation of the mixture may render the sample capable of reporting, or being analyzed for, whether or not a reaction, such as amplification, has occurred, on a target-by-target basis, and optionally the extent of any such reaction.

Providing Partitions.

Partitions for the assay may be provided, indicated at 54. Each partition may include a portion of a same mixture. In some cases, the portion may constitute the entire partition. The mixture may contain each target (e.g., provided by a same sample), each reporter, and/or one or more amplification reagents (e.g., a complete set of reagents for amplification of each target). Accordingly, the partitions, collectively, may contain a plurality of targets and each partition may contain the same generic reporter and optionally the same specific reporter. The targets may include at least one maskable target (interchangeably termed a masked target), and at least one obscuring target (interchangeably termed a masking target or a dominant target). The obscuring target is capable of at least partially masking the presence of one or maskable targets when a copy of each target is present in the same partition.

The partitions when provided (e.g., when formed) may contain each target at "partial occupancy," which means that each partition of only a subset of the partitions contains at least one copy of each target (and/or template) to be assayed. For example, with a multiplexed assay performed on a first target and a second target, only a first subset of the partitions contains the first target, and only a second subset of the partitions contains the second target. The first subset and the second subset of the partitions may be the same subset, if the first target and the second target are fully associated with and/or linked to each other when the partitions are formed. Alternatively, the first subset and the second subset of the partitions may be distinct if the first target and the second target are not fully associated with and/or linked to each other when the partitions are formed. In some cases, if the targets are not fully associated and/or linked, each partition of a distinct third subset of the partitions may contain at least one copy of each target. Accordingly, with partial occupancy, one or more (e.g., a plurality) of the partitions contain no copies of the first target, one or more (e.g., a plurality) of the partitions may contain a single copy (only one copy) of the first target, and, optionally, yet one or more of the partitions (e.g., the rest of the partitions) may contain two or more copies of the first target. Similarly, with partial occupancy, one or more (e.g., a plurality) of the partitions contain no copies of the second target, one or more (e.g., a plurality) of the partitions may contain a single copy (only one copy) of the second target, and, optionally, yet one or more of the partitions (e.g., the rest of the partitions) may contain two or more copies of the second target.

The term "partial occupancy" is not restricted to the case where there is no more than one copy of a particular template/target of interest in any partition. Partitions containing a template and/or a target at partial occupancy may, for example, contain an average of more than, or less than, about one copy, two copies, or three copies, among others, of the template/target per partition when the partitions are provided or formed. Copies of a template (and/or target) may have a random distribution among the partitions, which may be described as a Poisson distribution. In some cases, a significant number of the partitions (e.g., at least about 1%, 2%, 5%, 10%, or 20%, among others, of the partitions) may contain a copy of each of at least two targets, and/or a plurality of the partitions each may contain at least one copy of all targets.

Targets may be unlinked, partially linked, or fully linked when partitions are formed. Linked targets may be attached to each other covalently and/or by base pairing.

Each target may be an analyte on interest (e.g., a nucleotide sequence of interest) or a surrogate therefor (e.g., a nucleic acid bound to and/or corresponding to a nucleotide sequence of interest). The target may be nucleic acid that includes a sequence of nucleotides. The target, if nucleic acid, may be single-stranded or double-stranded, among others. A nucleic acid target may be provided by a template, with the target forming at least a portion or all of the template. The target may correspond to an amplicon produced by amplification. The amplicon may be single-stranded or double-stranded, among others. In some cases, the target may be or correspond to an analyte that is not nucleic acid, such as a small molecule, a polypeptide, a lipid, an amino acid, an ion, or the like.

The partitions may be provided by distributing or separating portions of a sample-containing bulk phase into partitions. Any suitable fraction including up to all of the bulk phase may be distributed to the partitions. Each partition may be and/or include a fluid volume that is isolated from the fluid volumes of other partitions. The partitions may be isolated from one another by a fluid phase, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with at least one droplet generator, by agitation of the sample (e.g., shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 pL, among others.

The partitions, when initially formed, may be competent for performance of one or more reactions in the partitions. Alternatively, one or more reagents may be added to the partitions after they are formed, to provide partitions competent for reaction. The reagents may be added by any suitable mechanism, such as a fluid dispenser, fusion of partitions/droplets, or the like.

Performance of Reactions.

A reaction corresponding to each target may be performed in the partitions, indicated at 56. The reaction may be an enzyme-catalyzed reaction. The reaction may produce a product, which may increase linearly or exponentially, among others, during the reaction.

The reaction for each target may be an amplification reaction that amplifies copies of the target present in individual partitions. Amplification of each target may occur selectively in partitions containing at least one copy of the target (e.g., containing at least one copy of a template that includes the target). Amplification may be linear or exponential, among others.

Amplification may or may not be performed isothermally. In some cases, amplification in the partitions may be encouraged by heating the partitions and/or incubating the partitions at a temperature above room temperature, such as at a denaturation temperature, an annealing temperature, and/or an extension temperature, for one or a plurality of cycles. In some examples, the partitions may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Data Collection.

Data may be collected from the reporters in the partitions, indicated at 58. The partitions may contain only one reporter or a plurality of different reporters having any suitable structure and characteristics. Each reporter may be a specific reporter (e.g., a probe) or a generic reporter (e.g., an intercalating dye). In some cases, at least one specific reporter may report on the occurrence of only one particular reaction and thus only one target in a multiplexed assay. In other cases, a specific reporter may report on the occurrence of two or more reactions and thus two or more targets. Each reporter interchangeably may be termed a reaction reporter and/or an amplification reporter.

A specific reporter binds with substantial specificity to a product (e.g., an amplicon) of a reaction, based on an identity of the product, to the substantial exclusion of other structurally different substances of the same class as the product. For example, each specific reporter may bind to a particular sequence or site to the substantial exclusion of other sequences or sites. The specific reporter may include or be a probe including at least one nucleic acid (e.g., at least one oligonucleotide) that binds specifically to a complementary nucleotide sequence present in a target and/or an amplicon corresponding to the target. The probe may include a label associated with an oligonucleotide (e.g., covalently attached or bound noncovalently, among others). The label may be optically detectable directly or indirectly. Accordingly, the label may be a luminophore (such as a photoluminescent moiety (e.g., a fluorophore or phosphor)), an enzyme (e.g., a peroxidase, beta-galactosidase, alkaline phosphatase, phosphodiesterase, or the like), a member of a specific binding pair (e.g., biotin or avidin/streptavidin), or an epitope tag, among others. A probe including a luminophore may or may not also include an energy transfer partner for the luminophore, such as a quencher or another luminophore (e.g., to produce luminescence resonance energy transfer (e.g., FRET)). The probe may or may not also function as a primer that is extended in the assay. Exemplary labeled probes include TaqMan® probes, Scorpion® probes/primers, Eclipse® probes, Amplifluor® probes, molecular beacon probes, Lux® primers, proximity-dependent pairs of hybridization probes that exhibit FRET when bound adjacent one another on an amplicon, QZyme® primers, or the like.

The specific reporter may have distinct forms or states. The specific reporter may have an initial/intact form or state and one or more degraded/modified forms or states. The one or more degraded/modified forms or states may be produced from the initial/intact form during amplification of the second target. The forms or states may be distinguishable optically. For example, the degraded/modified form may be more or less photoluminescent than the initial/intact form.

A generic reporter (interchangeably termed a nonspecific reporter) binds without substantial specificity to a product of a reaction (e.g., an amplicon), such that other structurally different substances of the same class as the product (e.g., other amplicons of unrelated sequence) can also be bound by the reporter. The nonspecific binding may not depend on a unique feature of the arrangement of atoms of one or both of the reporter and the product (e.g., the target and/or amplicon). Multiple copies of the generic reporter may be capable of binding to a single copy of a reaction product, for example, with the number of copies bound being related directly, such as proportional, to the amount or length of the reaction product. For example, the generic reporter may be a photoluminescent dye that binds to nucleic acid relatively nonspecifically. The dye may not be attached to an oligonucleotide that confers substantial sequence binding specificity. The dye may be a major groove binder, a minor groove binder, an intercalator, or an external binder, among others. The dye may bind preferentially to double-stranded relative to single-stranded nucleic acid and/or may exhibit a greater change in a photoluminescence characteristic (e.g., emission intensity) when bound to double-stranded relative to single-stranded nucleic acid. Exemplary dyes that may be suitable include luminescent cyanines, phenanthridines, acridines, indoles, imidazoles, and the like, such as DAPI, Hoechst® 33258 dye, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others.

R targets may be assayed in a multiplex assay, and the data may be collected in less than R optical channels (e.g., in different wavebands). In other words, the number (R) of targets assayed may be greater than the number of optical channels used for detecting the target-specific reactions. In some cases, the data may be collected in only one or two optical channels, or in at least two, three, or more optical channels, among others. In some cases, data may be collected from the same number of optical channels as targets in the assay. An optical channel interchangeably may be termed a detection channel.

An optical channel may represent a particular detection regime with which emitted light is generated and detected. The detection regime may be characterized by a spectral content (i.e., a wavelength regime) for detection of emitted light. If pulsed excitation light is used in the detection regime to induce light emission, the detection regime may be characterized by a spectral content (a wavelength(s) or waveband(s)) for illumination with excitation light and/or a time interval during which light emission is detected with respect to each light pulse. Accordingly, optical channels that are different from each other may differ with respect to the spectral content (wavelength(s)/waveband(s)) of excitation light, with respect to the spectral content (wavelength(s)/waveband(s)) of emitted light that is detected, and/or with respect to the time interval during which emitted light is detected relative to each pulse of excitation light, among others.

Data collection may include generating one or more signals representative of detected light. The signal may represent an aspect of light, such as the intensity of the light, detected in the same optical channel from one or more reporters for two or more distinct targets. The signals optionally may include data collected in two or more different optical channels (e.g., at different wavelengths and/or different wavelength ranges (wavebands) and/or color regimes) from reporters for the same and/or different targets). The light detected from each reporter may be light emitted from a luminophore (e.g., a fluorophore). The light detected in a given channel may be detected such that light from different reporters is summed or accumulated without attribution to a particular reporter. Thus, the signal for a given channel may be a composite signal that represents two, three, four, or more reporters and/or assays and two, three, four, or more targets.

The signal(s) may be created based on detected light emitted by the generic reporter, and optionally from one or more other reporters in the partitions. The one or more other reporters may report whether at least one of two or more particular amplification reactions represented by the signal has occurred in a partition and thus whether at least one copy of at least one of two or more particular targets corresponding to the two or more particular amplification reactions is present in the partition. The level or amplitude of the signal corresponding to the reporters may be analyzed to determine whether or not at least one of the particular reactions has occurred and at least one copy of one of the particular targets is present. The level or amplitude of the signal may vary among the partitions according to whether at least one of the particular reactions occurred or did not occur and at least one of the particular targets is present or absent in each partition. For example, a partition positive for a particular target may produce a signal level or amplitude that is above a given threshold and/or within a given range. Partitions may be analyzed and signals created at any suitable time(s). Exemplary times include at the end of an assay (endpoint assay), when reactions have run to completion and the data no longer are changing, or at some earlier time, as long as the data are sufficiently and reliably separated.

Data may be collected from a plurality of the partitions (i.e., only a subset or all of the partitions) under any suitable conditions. All of the data may be collected at about the same temperature from the plurality of partitions, at a temperature that is below a melting temperature of each amplicon, and/or below about 50 degrees Celsius, among others. The amplification data may be collected after an endpoint of amplification has been reached for each target.

Partition clusters each positive for at least one different combination of zero, one, or more of the targets may be identified. Generally, if masking occurs, only a subset of all possible combinations may be identified and some of the clusters may contain two or more populations having distinct target compositions. Identification may be performed by a data processor using an algorithm (e.g., an algorithm that identifies patterns (e.g., partition clusters) in the data), by a user, or a combination thereof. In some cases, a data processor may produce and output (e.g., display) a plot of the collected data (e.g., a 2-D scatter plot or histogram, or, with three or more optical channels for detection, two or more 2-D scatter plots or histograms with different pairs of axes). The user then may define the boundary of each cluster based on the plot(s), e.g., through a graphical user interface to define population boundaries, and/or by inputting values (e.g., representing intensity ranges) to define a boundary for each cluster. Each cluster boundary may be defined by one or more ranges of values, a geometrical shape that surrounds the cluster (e.g., a polygon, ellipse, etc.), or the like. Further aspects of cluster identification are presented below in Sections II-V.

The reaction components and/or conditions of any of the multiplexed assays disclosed herein may be adjusted to improve the resolution of different partition populations in the data. By changing the concentration of a particular assay within a multiplexed assay, the reaction efficiency for a particular target can be affected, which may result in a difference in signal level that allows populations detected with the same reporter and/or different reporters to be distinguished from one another. By changing reaction components/conditions, additional targets may be detected in the same multiplexed reaction. In some cases, the signal amplitude for a target may be adjusted by varying the concentration of one or both primers for the target. Varying primer concentration without changing the reporter concentration may be useful in assays where the same reporter (e.g., a probe or a generic reporter) is used to detect two or more targets, but each of the two targets is amplified with at least one different primer. In some cases, the signal amplitude for one or more targets may be adjusted by changing the annealing temperature used for thermocycling, the total concentration of dNTPs, the amounts of individual dNTPs relative to each other (e.g., if the two targets have substantially different base compositions), or the like.

A partition count for each partition cluster may be obtained. The partition count may be a value representing the number of partitions constituting a particular partition cluster.

A number of partitions that are positive (or negative) for each target may be determined from the collected data. The signal detected from each partition, and the partition itself, may be classified as being positive or negative for each of the reactions/targets contributing to the signal. Classification may be based on the strength (and/or other suitable aspect) of the signal. For example, classification may be based on the intensity of light detected from the partition in a single optical channel or in two or more optical channels. If the signal/partition is classified as (testing) positive (+), for a given target, the reaction corresponding to that target is deemed to have occurred and at least one copy of the target is deemed to be present in the partition. In contrast, if the signal/partition is classified as negative (−), for a given target, the reaction corresponding to that target is deemed not to have occurred and no copy of the target is deemed to be present in the partition (i.e., the target is deemed to be absent from the partition).

The data including all combinations of targets (i.e., all combinations of the presence or absence of each of the targets) will generally represent $2^R$ populations each having a different target content, where R is the number of different targets. For example, with three targets (A-C, R=3), there are eight populations: ( ), (A), (B), (C), (AB), (AC), (BC), and (ABC), each having a different target content. If target masking occurs, some of the populations will overlap and/or will not be distinguishable from one another as well-resolved clusters. Instead, some of the populations may overlap one another to form at least one heterogeneous cluster having a heterogeneous target content of one or more of the targets. Accordingly, less than $2^R$ well-resolved clusters may be produced with target masking and/or with other assay configurations as described elsewhere in the present disclosure.

Determination of Target Concentrations.

A concentration of each target may be determined, indicated at 60. The concentration of at least one of the targets may be determined from only a subset of the collected data. For example, the concentration of at least one masked target may be determined from only a subset of the data. The subset of data may selectively exclude partitions that are positive for an obscuring target that at least partially obscures the presence of the masked target in partitions containing a copy of both targets.

Any suitable subset of the partitions may be excluded, for calculating the concentration of a given target, without skewing the concentration determined, if the basis for exclusion is independent of the presence/absence of the target. For example, in an assay of targets A and B, all (or any suitable subset of) B-positive partitions may be excluded from calculation of the concentration for target A, if being positive for B is independent of the presence or absence or A. (For example, there is no substantial association or linkage between targets A and B when partitions are formed.) Accordingly, if all B-positive partitions are present in the same cluster (or two or more clusters), the entire cluster (or the two or more clusters) can be excluded from the calculation of the concentration of target A, without skewing the result. As another example, in an assay for unlinked targets A, B, and C, the concentration of target A can be determined with all B-positives and all C-positives excluded, with only B-positives or only C-positives excluded, or with any combination of B-positives and C-positives excluded that is independent of the presence/absence of A (e.g., all BC-positives, whether A-negative or A-positive). In the same assay, the concentration of target B (or target C) may be determined from all of the data, if all B-positives (or all C-positives) are resolved from all other populations lacking a copy of target B (or target C). Alternatively, the concentration of target B (or target C) may be determined from only a subset of the data that excludes partitions independent of the presence/absence of B (or C).

Determination of target concentrations may (or may not) be based on each target having a Poisson distribution among the partitions. Each concentration may, for example, be a value representing the average number copies of the target per partition. The partition data further may be used (e.g., directly and/or as concentration data) to estimate copy number (CN) and copy number variation (CNV), using any suitable algorithms.

A level, such as a concentration, of each target may be determined with Poisson statistics. The concentration of the target in the partitions may be calculated from the fraction of partitions that are positive for the target (or, equivalently, the fraction of partitions that are negative for the target) by assuming that copies of the target (before amplification) have a Poisson distribution among the partitions. With this assumption, the fraction f(k) of partitions having k copies of the target is given by the following equation:

$$f(k) = \frac{\lambda^k}{k!} e^{-\lambda} \quad (1)$$

Here, $\lambda$ is the concentration of the target in the partitions, expressed as the average number of target copies per partition (before amplification). Simplified Poisson equations may be derived from the more general equation above and may be used to determine target concentration from the fraction of positive partitions. An exemplary Poisson equation that may be used is as follows:

$$\lambda = -\ln\left(1 - \frac{N_+}{N_{tot}}\right) \quad (2)$$

where $N_+$ is the number of partitions (i.e., the partition count) positive for a given target, and where $N_{tot}$ is the total number of partitions that are positive or negative for the target. $N_{tot}$ is equal to a sum of (a) $N_+$ for the target and (b) the number of partitions negative for the target, or $N_-$. $N_+/N_{tot}$ (or $N_+/(N_+ + N_-)$ is equal to $f_+$, which is the fraction of partitions positive for the target (i.e., $f_+ = f(1) + f(2) + f(3) + \ldots$) (see Equation 1), and which is a measured estimate of the probability of a partition having at least one copy of the target. Another exemplary Poisson equation that may be used is as follows:

$$\lambda = -\ln\left(\frac{N_-}{N_{tot}}\right) \quad (3)$$

where $N_-$ and $N_{tot}$ are as defined above. $N_-/N_{tot}$ is equal to $f_0$, which is the fraction of negative partitions (or $1-f_+$), is a measured estimate of the probability of a partition having no copies of the target, and $\lambda$ is the target concentration as described above.

Equations 2 and 3 above can be rearranged to produce the following:

$$\lambda = \ln(N_{tot}) - \ln(N_{tot} - N_+) \quad (4)$$

Equations 2 and 3 above can be rearranged to produce the following:

$$\lambda = \ln(N_{tot}) - \ln(N_-) \quad (5)$$

The concentration of each target in a multiplexed assay can, for example, be determined with any of Equations 2-5, using values (i.e., partition counts) obtained for $N_{tot}$ and $N_-$ or $N_+$, for each target. In some cases, the value used for $N_{tot}$ (the total partition count) may be the same for each target. In other cases, the value used for $N_{tot}$ may vary, such as if some of the populations are excluded from the total count due to population overlap (target masking). In some embodiments, $N_{tot}$ may be equivalent to a combination of all populations, namely, a sum of the partition counts for all populations identified.

The value used for $N_-$ or $N_+$ is generally different for each target, and may result from summing the counts from a plurality of partition populations each containing a different combination of the targets being tested in the multiplexed assay. For example, with three targets (A, B, and C) in a multiplexed assay, the number of partitions positive for target A, $N_{+A}$, may be calculated as the sum of counts from the single (A only), double (AB and AC), and triple (ABC) positive populations, for use in Equation 2 or 4. Equivalently, the number of partitions negative for target A, $N_{-A}$, may be calculated, for use in Equation 3 or 5, as the difference between $N_{tot}$ and $N_{+A}$. Alternatively, the number of partitions negative for A may be calculated as the sum of counts from each population that is negative for target A, namely, in this example, a triple negative ("empty") population, two single positive populations (B and C), and one double positive population (BC). The same process may be repeated for each of the other targets using partition counts from the appropriate subset of populations.

In some embodiments, an estimate of the level of the target may be obtained directly from the positive fraction, without use of Poisson statistics. In particular, the positive fraction and the concentration (copies per partition) converge as the concentration decreases. For example, with a positive fraction of 0.1, the concentration is determined with Equation 2 to be about 0.105, a difference of only 5%; with a positive fraction of 0.01, the concentration is determined to be about 0.01005, a ten-fold smaller difference of only 0.5%. However, the use of Poisson statistics can provide a more accurate estimate of concentration, particularly with a relatively higher positive fraction, because the equation accounts for the occurrence of multiple target copies per partition.

FIG. 2 shows an exemplary system 70 for performing the digital assay of FIG. 1. System 70 may include a partitioning assembly, such as a droplet generator 72 ("DG"), a thermal incubation assembly, such as a thermocycler 74 ("TC"), a detection assembly (a detector) 76 ("DET"), and a data processing assembly (a data processor) 78 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets) or signals/data, between the assemblies. Any suitable combination of the assemblies may be operatively connected to one another, and/or one or more of the assemblies may be unconnected to the other assemblies, such that, for example, material/data are transferred manually.

Detector 76 may provide a plurality of optical channels in which data can be collected. The detector may have a distinct sensor or detection unit for each optical channel.

System 70 may operate as follows. Droplet generator 72 may form droplets disposed in a continuous phase. The droplets may be cycled thermally with thermocycler 74 to promote amplification of targets in the droplets. Signals may be detected from the droplets with detector 76. The signals may be processed by processor 78 to determine numbers of droplets and/or target concentrations, among others. The system may include a program, optionally residing on a computer-readable storage medium, and comprising instructions for causing the data processor and/or controller to perform and/or control any suitable combination of the steps disclosed herein, such as in FIG. 1.

Further aspects of sample preparation, partition formation (such as droplet generation), data collection, population identification and/or cluster assignment, obtaining partition counts, and target level determination, among others, that may be suitable for the system of the present disclosure are described in Sections II-V and in the references identified above under Cross-References, which are incorporated herein by reference.

II. DETERMINATION OF CONCENTRATION FOR MASKED AND MASKING TARGETS

Figure 4:
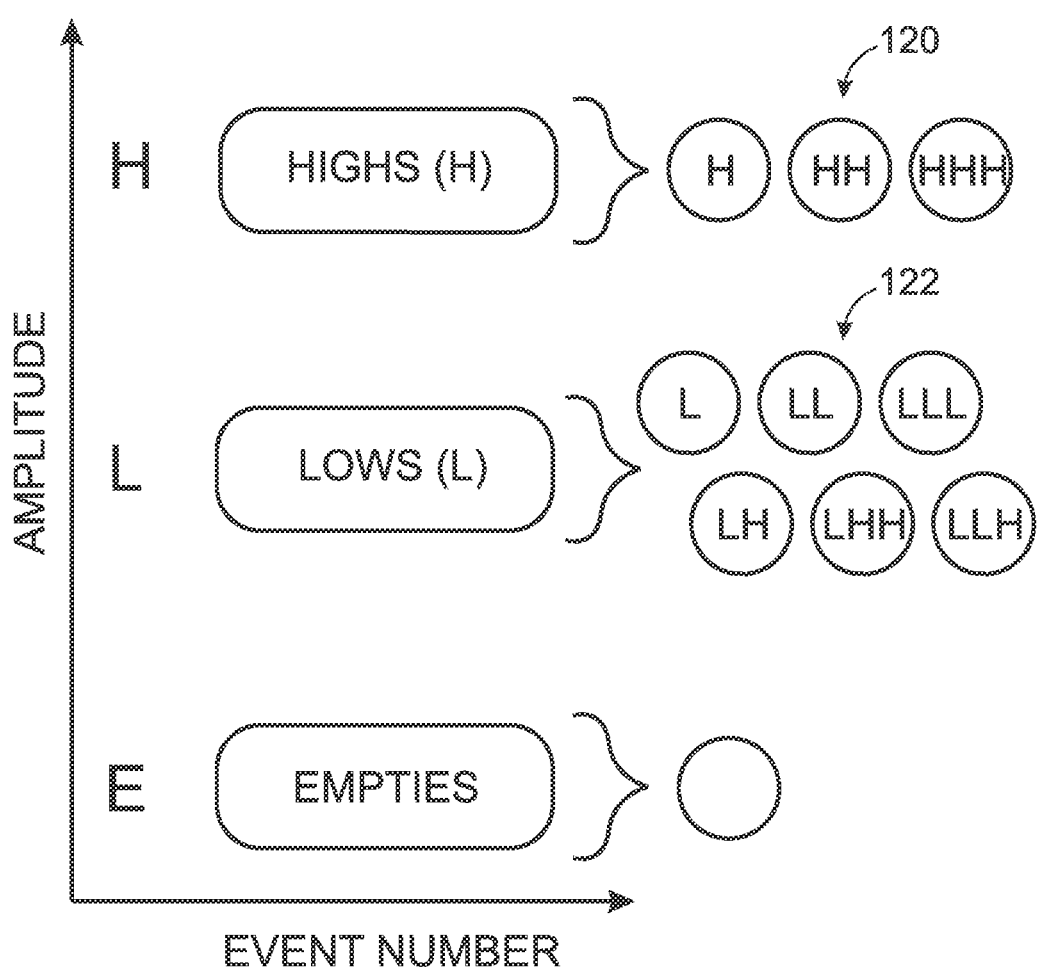
FIG. 4 is another schematic graph of multiplexed assay data that may be collected generally as in FIG. 3, but with the obscuring target (L) having a lower amplitude signal than the masked target (H), in accordance with aspects of the present disclosure.
Figure 5:
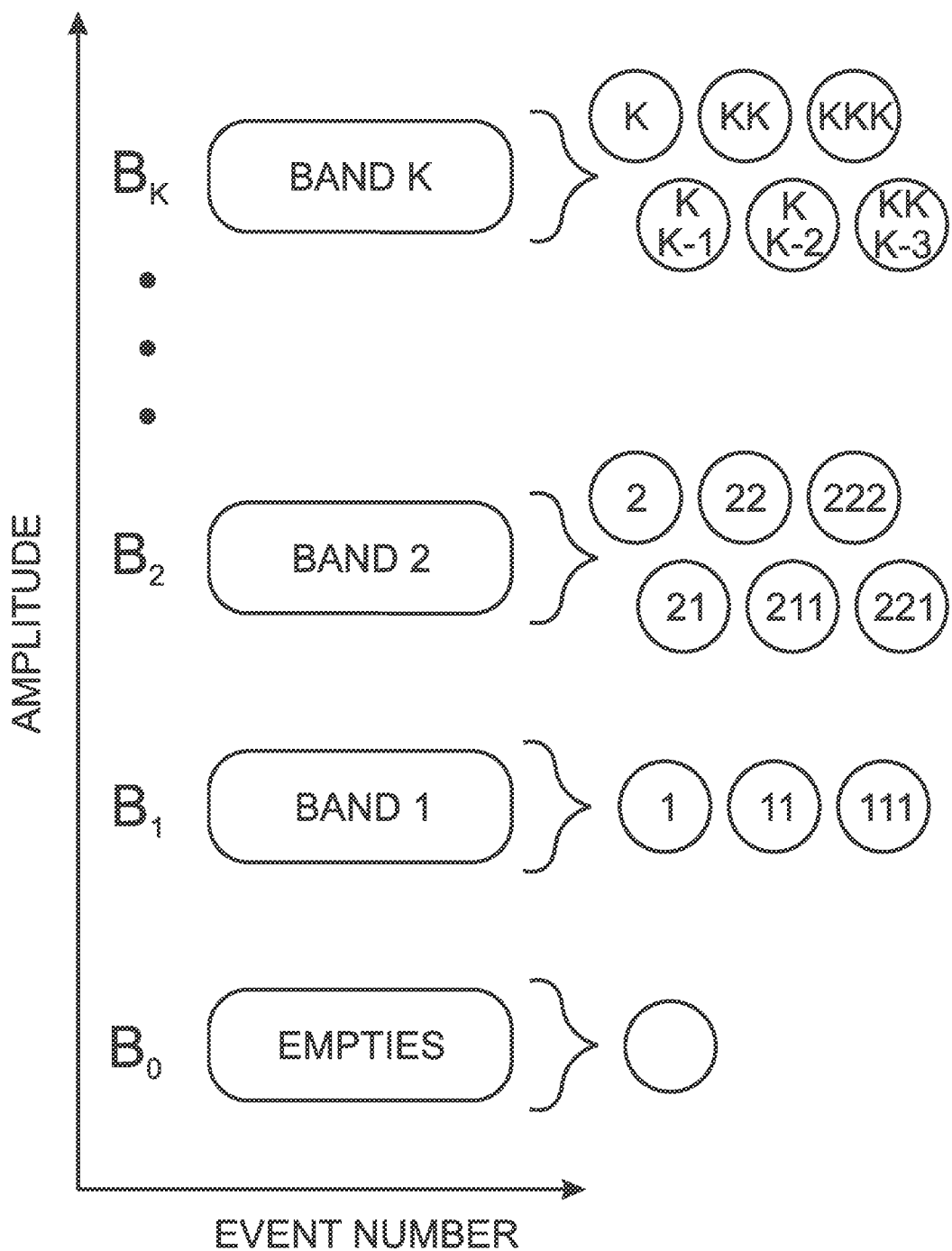
FIG. 5 is a schematic graph of multiplexed assay data that may be collected in a single detection channel from partitions, such as droplets, collectively containing K targets that mask one another serially according to a masking hierarchy, in accordance with aspects of the present disclosure.

This section describes exemplary approaches to determining target concentrations when target masking occurs and/or when partition populations overlap with one another in the collected data; see FIGS. 3-5.

In a typical duplex (two-target) assay performed with two or more optical channels for detection, the presence of different targets in the same partitions leads to signals in different channels. However, in some cases, only one detection channel may be utilized a duplex assay, which may cause one target to mask the detectability of another. For example, masking can occur when two amplicons of significantly different amplification efficiencies are produced in the same droplet and are detectable via the same generic reporter, such as a SYBR®-derived dye. The presence of the amplicon that accumulates more slowly can be masked by the amplicon that accumulates more quickly (e.g., see Example 2). Another example can be found in next-generation sequence (NGS) library formation. Products that only contain a pair of adapters without an insert may outcompete fully formed species and thus mask them in a single-channel assay (e.g., see Example 1). The present disclosure enables robust calculation of the concentration of a pair of competing targets that produce target masking.

In a single-channel assay, it may be possible to accurately measure the concentrations of multiple competing species provided: (1) the species produce different signal levels, (2) rank order masking or suppression of species exists, and (3) the signal is separated into a banding pattern allowing counting of partitions in bands. Examples of such situations in practice include variable size amplicons, such as mRNA versus precursor RNA, loci with small insertions or deletions, NGS library quantitation, or the like.

FIG. 3 shows a schematic graph of amplification data that may be collected in a single detection channel. The graph plots signal amplitude (e.g., photoluminescence intensity, such as fluorescence intensity) as a function of detected event number. Each event represents a spike or wave in signal strength caused by a detected partition 90 (such as a droplet 92 flowing through a detection region). The amplitude plotted for each partition/event may be a maximum signal value, an average signal value, or an integrated signal value, among others, for the corresponding spike or wave. The x-axis of FIG. 3 alternatively may be labeled as time or partition number, among others.

The partitions represented by the data of FIG. 3 collectively contain a masking target 94 ("H") and a masked target 96 ("L") that produce respective, characteristic higher and lower amplitude signals. When at least one copy of target H is present in a partition, the higher amplitude signal is dominant, as exemplified at 98 by a group of H-positive partitions. The higher amplitude signal is detected from each H-positive partition, whether or not a copy of target L also is present in the partition. In other words, the signal produced by amplification of target H masks the signal from amplification of target L, because target L does not sufficiently increase (or decrease) the signal amplitude over that generated by amplification of target H alone. In contrast, when one or more copies of target L alone are present in a partition (i.e., in the absence of any copies of target H), the lower amplitude signal is detected from the partition, as exemplified at 100 by a group of L-positive, H-negative partitions. Individual partitions, such as partition 102 that do not contain a copy of either target ("empties" or "negatives"; abbreviated "E") produce an even lower, baseline signal. Accordingly, three bands 104, 106, 108 of partitions are visible in the graph. (Bands interchangeably may be termed clusters.) Band 104 represents H-positive partitions (±L), band 106 represents L-positive partitions that are H-negative, and band 108 represents H- and L-negative partitions.

The number of partitions in each band can be determined (interchangeably termed counted), and the concentration of each target calculated using, for example, Equation 5 of Section I. However, the concentration of masked target L will be underestimated with this approach, if all of the partitions are included in the calculation. Accordingly, only a subset of the data can be utilized to determine the concentration of target L.

The general formula for calculating a concentration value (copies per partition (cpp)) of a particular factor (e.g., a single species or target, a combination of species or targets, etc.) is as follows:

$$\lambda_{factor} = \ln(N_{tot}) - \ln(N_{not\,factor}) \qquad (6)$$

where $\lambda_{factor}$ is the concentration in cpp of the factor, $N_{tot}$ is the total number of partitions observed, and $N_{not\,factor}$ is the number of partitions that do not exhibit the factor (which is written as $N_-$ in Equations 3 and 5).

Since all H-positive partitions are detectable, the following equation holds:

$$\lambda_H = \ln(N_E + N_L + N_H) - \ln(N_E + N_L) \qquad (7)$$

where $\lambda_H$ is the concentration of the masking target H, $N_E$ is the number of empty partitions, $N_H$ is the number of higher amplitude partitions, and $N_L$ is the number of lower amplitude partitions.

The presence of masked target L is independent of the presence of masking target H in a partition. Accordingly, the H-positive partitions are unbiased with respect to target L. In other words, the H-positive partitions can be excluded from the concentration calculation for masked target L. Stated differently, the concentration for target L computed from lower bands 106, 108 should be the same, absent statistical variation, as the concentration computed from all three bands (if the L target were not masked). Another way to explain this approach is that if the higher amplitude partitions for some reason became invisible, and only the lower amplitude and empty (negative) bands were visible, the concentration of target L still could be computed accurately as follows:

$$\lambda_L = \ln(N_E + N_L) - \ln(N_E) \qquad (8)$$

The total target concentration (i.e., the concentration of L or H) can be computed in two different ways. A first approach is as follows:

$$\lambda_{L\,or\,H} = \ln(N_E + N_L + N_H) - \ln(N_E) \qquad (9)$$

Alternatively, the two concentrations of targets L and H, calculated separately, can be summed:

$$\lambda_{L\,or\,H} = \lambda_H + \lambda_L \qquad (10)$$

Substitution with terms from Equations 7 and 8 produces the following:

$$\lambda_{L\,or\,H} = [\ln(N_E + N_L + N_H) - \ln(N_E + N_L)] + [\ln(N_E + N_L) - \ln(N_E)] \qquad (11)$$

Equation 11 simplifies to the following:

$$\lambda_{L\,or\,H} = \ln(N_E + N_L + N_H) - \ln(N_E) \qquad (12)$$

Therefore, both approaches give the same answer. In any event, more generally, the concentration of each masked target can be calculated from only a subset of the partitions that selectively excludes each population of partitions positive for an obscuring target that at least partially obscures the presence of the masked target.

Figure 3A:
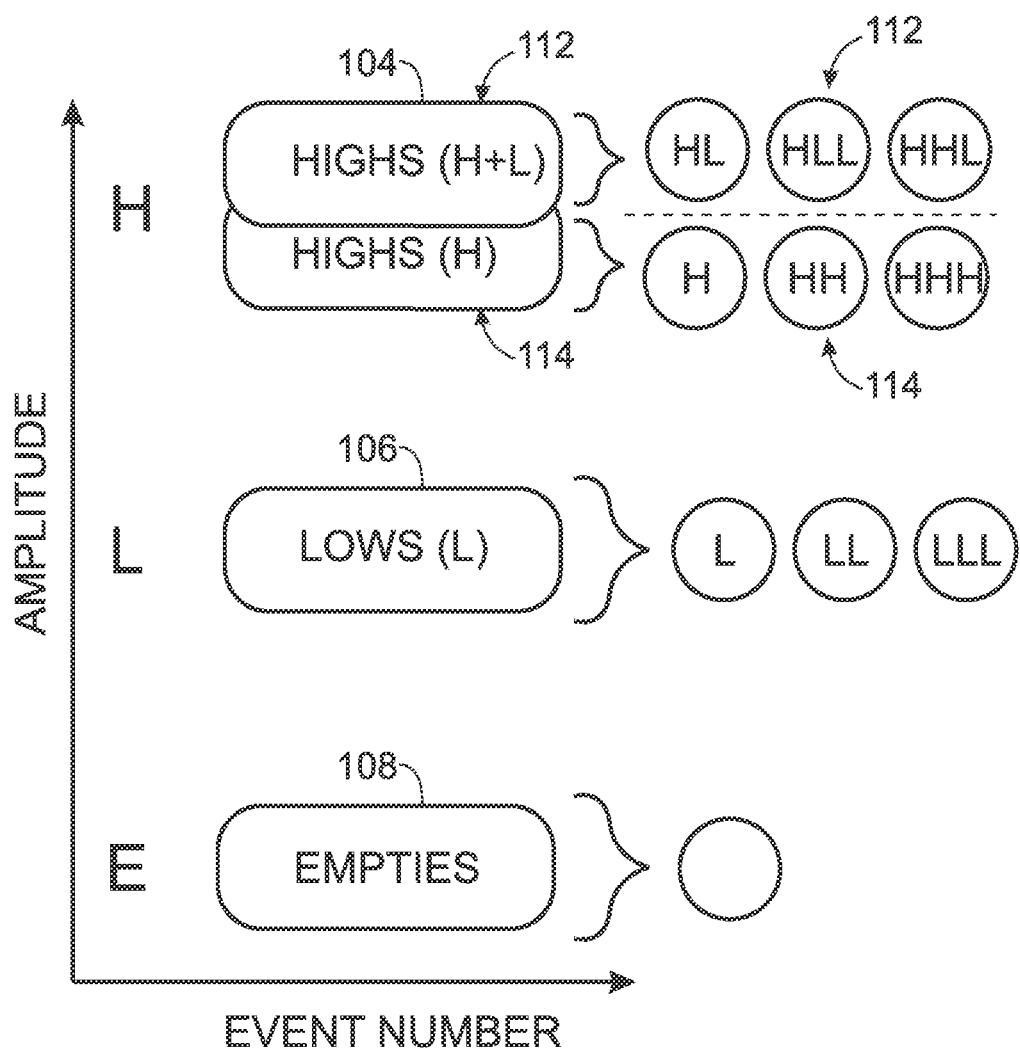
FIG. 3A is a schematic graph of multiplexed assay data that may be collected as in FIG. 3, but with the population of double-positive partitions (HL, HLL, etc.) exhibiting a small, detectable increase in signal amplitude over the population of partitions containing only target H, with the increase in signal amplitude being insufficient to resolve the two higher amplitude populations from each other, such that target L is still at least partially masked by the presence of target H, in accordance with aspects of the present disclosure.

FIG. 3A shows another schematic graph of data that may be collected as in FIG. 3. Here, a population 112 of double-positive partitions (H+L) exhibits a small, detectable increase in signal amplitude over a population 114 of single-positive partitions containing only target H. However, the increase in signal amplitude produced by a copy of the L target in population 112 is insufficient to fully resolve the two higher amplitude populations from each other. In other words, the partitions of each type, H+L and H-only, cannot be reliably distinguished from each other; the presence of target H in a partition at least partially masks the presence of target L. Accordingly, the concentration of target L can be determined more accurately by excluding both populations 112 and 114 from the set of partitions used for the calculation, as in Equation 8 above.

FIG. 4 shows another schematic graph of data that may be collected generally as in FIG. 3. Here, however, the masking target is target L, which has a lower amplitude signal, and the masked target is target H, which has a higher amplitude signal. As a result, detectably H-positive partitions 120 do not contain a copy of target L, while L-positive partitions 122 can contain no copies, or one or more copies of target H, in the same band or cluster of partitions.

The concentration of masked target H in FIG. 4 can be calculated in a manner analogous to Equation 8 above by excluding the L-positive partitions from the partition counts used in the calculation:

$$\lambda_H = \ln(N_E + N_H) - \ln(N_E) \qquad (13)$$

The concentration of target L in FIG. 4 can be calculated in a manner analogous to Equation 7 above, since target L is not masked and all L-positive partitions are detectable:

$$\lambda_L = \ln(N_E + N_L + N_H) - \ln(N_E + N_H) \qquad (14)$$

FIG. 5 shows a schematic graph of data that may be collected in a single detection channel from partitions, such as droplets, collectively containing k targets that mask one another serially according to a masking hierarchy. More particularly, the k targets can be rank-ordered from 1 to k such that the presence of a target of rank i in a partition masks the presence of each target with a lower rank (i.e., i–1, i–2, . . . , 1). Here, the signal from a target of rank i is stronger than from each target of lower rank, but any assignable order of signal amplitudes may be suitable. For example, in some cases, the signal amplitude of each successive target of higher rank may decrease relative to each target of lower rank (such that target k has a signal amplitude closest to the empty partitions), or the signal amplitudes may not monotonically increase or decrease according to the rank order.

The data for the partitions is distributed among k target-positive bands ($B_1, B_2, \ldots, B_k$) plus a band of empty/negative partitions of lowest amplitude ($B_0$). For each target-positive band of rank i, only partitions containing targets with rank i or lower, namely, i–1, i–2, . . . are present in the band (otherwise such a partition would move to a band of higher rank).

The correct concentration of all targets can be calculated using an inductive method. The concentration of each target can be "peeled off" with the following expressions, wherein $N_i$ is the number of partitions in band $B_i$:

$$\lambda_1 = \ln(N_0 + N_1) - \ln(N_0) \qquad (15)$$

$$\lambda_2 = \ln(N_0 + N_1 + N_2) - \ln(N_0 + N_1) \qquad (16)$$

And for the $i^{th}$ case:

$$\lambda_i = \ln(N_0 + N_1 + \ldots + N_i) - \ln(N_0 + N_1 + \ldots + N_{i-1}) \qquad (17)$$

This approach can be verified as in Equations 9 to 12 above:

$$\lambda_1 + \lambda_2 + \ldots + \lambda_k = \ln(N_0 + N_1 + \ldots N_k) - \ln(N_0) \qquad (18)$$

$$\lambda_{tot} = \ln(N_{tot}) - \ln(N_0) \qquad (19)$$

The single channel examples presented here may be extended to data collected in two or more detection channels (e.g., by detection of two or more distinct wavebands of emitted light in the channels; see Sections III and IV). In some cases, if the data are collected from channel-specific reporters, the data may be "collapsed" into a single channel for two or more targets that are multiplexed in that channel, by ignoring distinguishable populations produced by amplitude differences in the other detection channel(s).

III. EXEMPLARY ASSAY CONFIGURATIONS WITH TARGET MASKING

This section describes exemplary multiplexed assay configurations in which target masking can occur and/or partition populations of different target content in the data; see FIGS. 6-17. Data from any of the multiplexed assays can be processed as described in Section II, using data exclusion for calculating at least one level of a target.

Target masking may occur by any suitable mechanism. In some cases, masking may result from different efficiencies of amplification for two (or more) distinct targets in the same partition, with the more efficiently-amplified target (the dominant target) masking the less efficiently-amplified target (the maskable target). Competition between assays for dominant and maskable targets in the same partition may attenuate or eliminate the signal change normally detected for assay of the maskable target in a partition, in the absence of the dominant target. In other words, the competition may prevent the maskable target assay from reaching its usual endpoint. The dominant target, by outcompeting the maskable target, may deplete or monopolize a limiting reagent required for the assay of both targets. The limiting reagent may be a primer used for amplification of both targets, a reporter that binds to amplicons for both targets, one or more dNTPs (and/or NTPs), an amplification enzyme that loses substantial activity during the assay, or the like. Alternatively, or in addition, the dominant target, by outcompeting the maskable target, may produce an inhibitory product, such as nucleic acid (e.g., an amplicon) at a sufficient concentration to inhibit amplification, to prevent the maskable target assay from reaching its usual endpoint. In some cases, masking may occur without substantial competition between targets.

Figure 6:
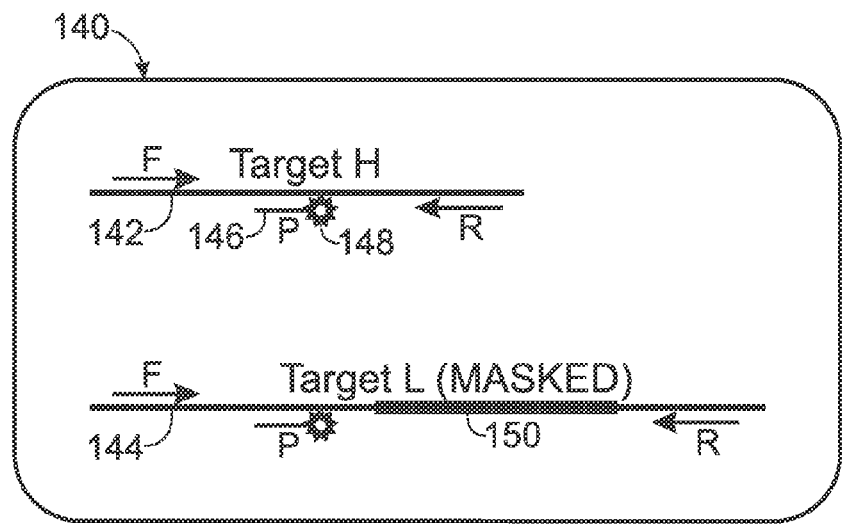
FIG. 6 is a schematic view of a partition from an exemplary multiplexed digital assay capable of generating the data of FIG. 3, with the partition containing a copy of a masking target (H) and a copy of a masked target (L) of different length, each amplifiable at a different efficiency with the same pair of forward (F) and reverse (R) primers and detectable via the same probe (P), in accordance with aspects of the present disclosure.

FIG. 6 shows a partition 140 from an exemplary multiplexed digital assay capable of generating the data of FIG. 3. The multiplexed assay is configured to perform individual assays for two targets, namely, a dominant target H and a masked target L. Partition 140 contains a copy of each target, with each copy provided by a respective template 142, 144, which may be single-stranded or double-stranded. (Other partitions in the assay will contain only target H, only target L, or neither target.) The templates have the same sequence as one another, as indicated by regions with the same line weight, which allows both templates to be bound specifically by the same pair of forward and reverse primers (F and R) and by the same probe (P). Accordingly, a signal from both target assays can be detected in the same detection channel. Here, the probe includes a nucleic acid 146 (an oligonucleotide) that is labeled with a luminophore 148 (e.g., a fluorophore), to produce a luminescence signal. The probe also may include a quencher that quenches photoluminescence from the luminophore, until the quencher and luminophore are spaced farther apart (e.g., by degradation of the probe and/or hybridization of the probe to an amplicon, among others).

Template 144 is longer than template 142 due to the presence of an additional sequence 150 located between the primer binding sites and not present in template 142. (Sequence 150 is represented by as a thicker line segment.) As a result, amplification of target H, relative to target L, produces a shorter amplicon, which causes amplification of target H to proceed more efficiently than amplification of target L. The presence of target L is masked in the partition. Data from the assay can be processed as described in Section II.

Figure 7:
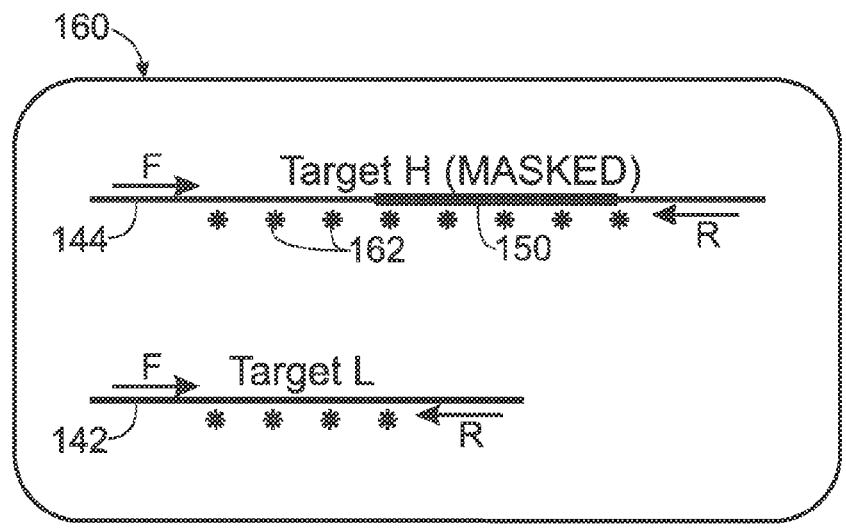
FIG. 7 is a schematic view a partition from an exemplary multiplexed digital assay capable of generating the data of FIG. 4, with the partition containing a copy of a masking target (L) and a masked target (H) of different length, each amplifiable at a different efficiency with the same pair of forward (F) and reverse (R) primers and detectable via the same generic reporter for amplicons (e.g., an intercalating dye), in accordance with aspects of the present disclosure.

FIG. 7 shows a partition 160 from an exemplary multiplexed digital assay capable of generating the data of FIG. 4. The multiplexed assay is configured to perform individual assays for two targets, namely, a dominant or masking target L and a masked target H. Partition 160 is similar to partition 140 of FIG. 6 except that the probe (P) has been replaced with a generic reporter 162, such as an intercalating dye, that photoluminesces more strongly when bound to double-stranded nucleic acid (e.g., amplicon). (Reporter 162 interchangeably may be termed a dye.) Light emission from dye 162 may be detected in a single optical channel or two or more optical channels.

Copies/molecules of dye 162 may bind to amplicon in a length-dependent manner, such that more copies of the reporter bind to a copy of the longer amplicon generated from template 144, relative to a copy of the shorter amplicon generated from template 142. As a result, amplification of target from template 144, in the absence of template 142, generates a higher intensity fluorescence signal than target amplification from template 142 (i.e., template 144 now corresponds to target H and template 142 to target L (compare with FIG. 6)). However, the shorter target masks the longer target, as described for FIG. 6, so target H is the masked target in this assay configuration. (Also see Example 2 of Section V.)

Figure 8:
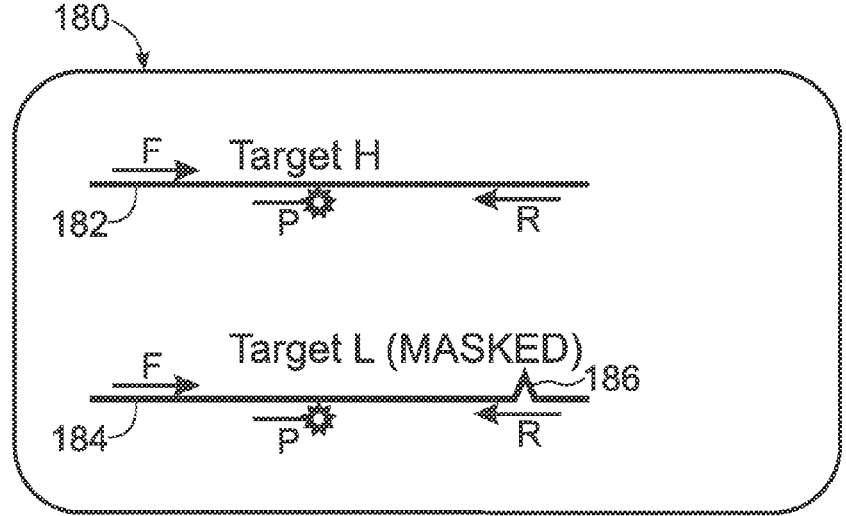
FIG. 8 is a schematic view of a partition from another exemplary multiplexed digital assay capable of generating the data of FIG. 3, with the partition containing a copy of a masking target (H) and a copy of a masked target (L) of the same length, each amplifiable at a different efficiency with the same pair of forward (F) and reverse (R) primers and detectable via the same probe (P), in accordance with aspects of the present disclosure.

FIG. 8 shows a partition 180 from another exemplary multiplexed digital assay capable of generating the data of FIG. 3. The partition contains a copy of a template 182 for a dominant target H and a copy of a template 184 for a maskable target L. Templates 182 and 184 have the same sequence except for a sequence variation 186, such as a single nucleotide difference, in the respective primer binding sites for the reverse primer (R). More particularly, the reverse primer forms a perfect duplex with template 182 and a mismatched duplex with template 184. As a result, target H is amplified more efficiently than target L, which masks the presence of target L when both targets are present in the same partition. The amplification inefficiency caused by the mismatched reverse primer also causes a lower detected signal for target L in the absence of target H.

Figure 9:
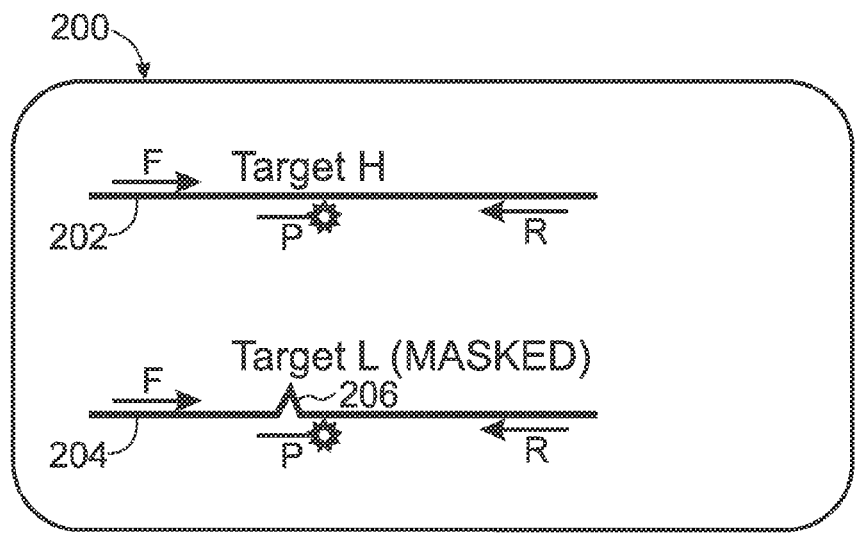
FIG. 9 is a schematic view of a partition from yet another exemplary multiplexed digital assay capable of generating the data of FIG. 3, with the partition containing a copy of a masking target (H) and a copy of a masked target (L) of the same length, each amplifiable at the same efficiency with the same pair of forward (F) and reverse (R) primers and detectable at different efficiencies via the same probe (P), in accordance with aspects of the present disclosure.

FIG. 9 shows a partition 200 from yet another exemplary multiplexed digital assay capable of generating the data of FIG. 3. The partition contains a copy of a template 202 for a dominant target H and a copy of a template 204 for a maskable target L. Templates 202 and 204 have the same sequence except for a sequence variation 206, such as a single nucleotide polymorphism, in the respective probe binding sites for the probe (P). More particularly, the probe forms a perfect duplex with an amplicon for target H and a mismatched duplex with an amplicon for target L. As a result, targets H and L are amplified with the same efficiency, but the probe binds more efficiently to amplicon for target H relative to the amplicon for target L, which masks the presence of target L, when both are present in the same partition. The binding inefficiency caused by the mismatched probe also causes a lower signal for target L in the absence of target H.

Figure 10:
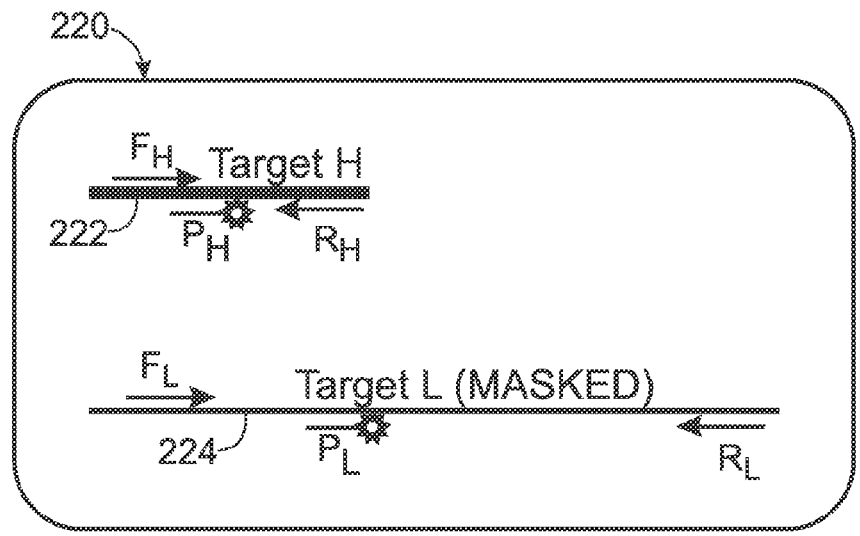
FIG. 10 is a schematic view of a partition from still yet another exemplary multiplexed digital assay capable of generating the data of FIG. 3, with the partition containing a copy of an obscuring target and a copy of a masked target, each amplifiable at a different efficiency with a different pair of forward and reverse primers ($F_H$ and $R_H$ or $F_L$ and $R_L$) and detectable via different probes ($P_H$ and $P_L$), in accordance with aspects of the present disclosure.

FIG. 10 shows a partition 220 from an exemplary multiplexed digital assay capable of generating the data of FIG. 3. Partition 220 contains a copy of a template 222 for target H and a copy of a template 224 for target L. Targets H and L are composed of different sequences, as represented by a thicker template 222 and a thinner template 224. Accordingly, targets H and L are amplified by different pairs of primers ($F_H$ and $R_H$ or $F_L$ and $R_L$), with amplification reported by different probes ($P_H$ and $P_L$). Target H is shorter than target L and is amplified substantially more efficiently, which gives target H a higher endpoint signal and can make target H dominant to target L.

Figure 11:
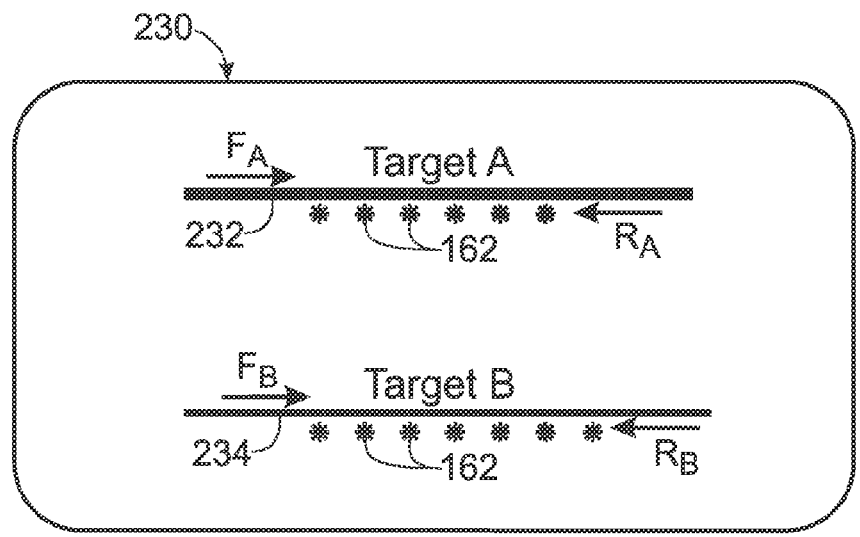
FIG. 11 is a schematic view of a partition from an exemplary multiplexed digital assay performed with a single detection channel, with the partition containing a copy of target A and target B, each amplifiable with a different pair of forward and reverse primers ($F_A$ and $R_A$ or $F_B$ and $R_B$) and detectable via a generic reporter (e.g., an intercalating dye), in accordance with aspects of the present disclosure.

FIG. 11 shows a partition 230 from an exemplary multiplexed digital assay performed with a single detection channel. The partition contains a copy of target A, which may be maskable, and a copy of target B, which may at least partially mask the presence of target A, or vice versa, according to reaction conditions (e.g., relative primer concentrations and/or the annealing temperature for primer hybridization, among others). The targets are composed of different sequences, as represented by a thicker template 232 and a thinner template 234 for the targets. The targets are amplified with different respective pairs of forward and reverse primers ($F_A$ and $R_A$ or $F_B$ and $R_B$). Amplification is reported for both targets by the same generic reporter 162 (e.g., an intercalating dye).

Figure 11A:
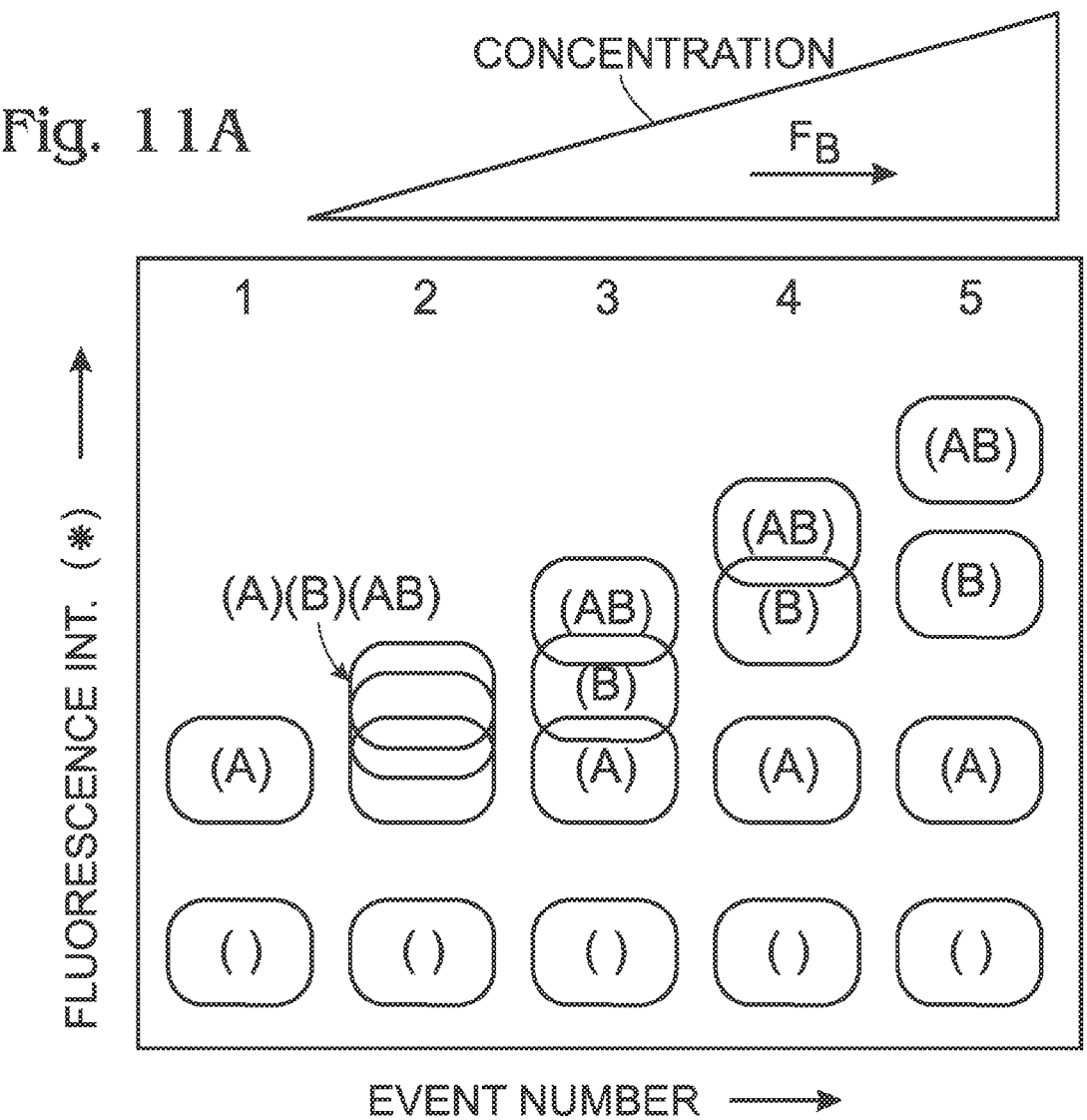
FIG. 11A is a schematic graph of fluorescence amplitude data that may be collected from five sets of partitions (lanes 1-5) in a single detection channel for the multiplexed digital assay of FIG. 11, with each set containing the same concentrations of targets A and B, forward primer A, and reverse primers A and B, and a variable concentration of forward primer B for target B, in accordance with aspects of the present disclosure.

FIG. 11A shows a schematic graph of fluorescence intensity data that may be collected from five sets of partitions (lanes 1-5) in a single detection channel for the multiplexed assay of FIG. 11. Each set contains the same concentrations of targets A and B, forward primer A, and reverse primers A and B, and a variable concentration of forward primer B for target B.

Lane 1 represents signal detected from generic reporter 162 binding to the amplicon for target A only; target B exhibits no amplification in lane 1 due to the absence of forward primer B. A partition population (here, a band (A)) containing target A only has an increased signal amplitude and is well separated from the negative partitions, indicated by ( ).

Lanes 2 and 3 represent signal detected with lower concentrations of forward primer B. The three target-positive bands (A, B, and AB) form a single cluster, with the constituent populations not resolved from each other. The position of the band for target A may (or may not) change (e.g., decrease in amplitude) due to competition with target B. However, the band for target A is shown here with the same position in all lanes, to simplify the presentation.

Lanes 4 and 5 show B-positive bands resolved from the band for target A. In lane 4, the two B-positive populations overlap. The data from lane 4 may be utilized to determine the concentrations of both targets as described above for FIG. 3. In particular, all of the lane 4 data may be utilized to calculate the concentration of target B, and only the lowest two bands to calculate the concentration of target A. In lane 5, all four populations are resolved, which allows all of the target 5 data to be used for calculation of the concentration of each target. In other cases, the concentrations of at least a pair of primers (e.g., both $F_B$ and $R_B$ for target B), the annealing temperature, and/or the like, may be adjusted to provide sufficient resolution of the A-only population from at least one other target-positive population.

Figure 12:
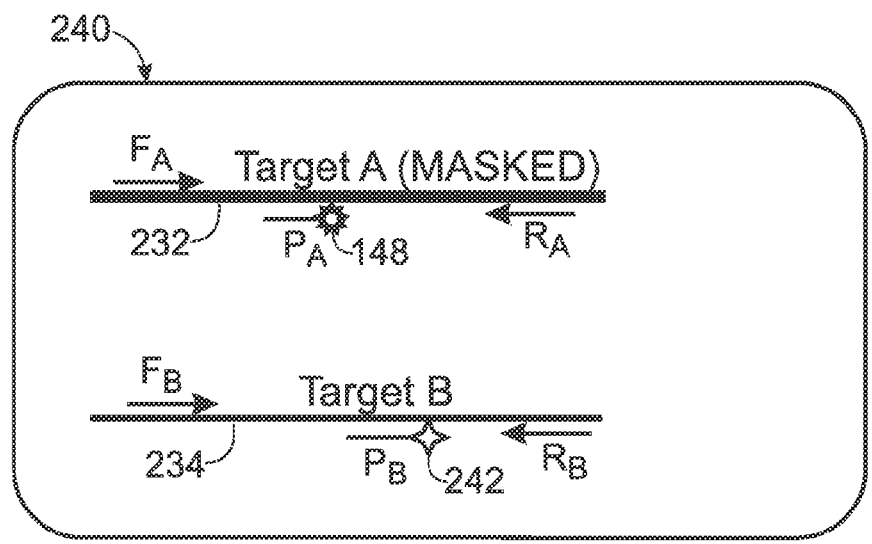
FIG. 12 is a schematic view of a partition from an exemplary multiplexed digital assay performed with two detection channels, with the partition containing a copy of a masked target A and a copy of a masking target B, each amplifiable at a different efficiency with a different pair of forward and reverse primers ($F_A$ and $R_A$ or $F_B$ and "$R_B$") and detectable via different probes ($P_A$ and $P_B$) having different fluorophore labels, in accordance with aspects of the present disclosure.

FIG. 12 shows a partition 240 from an exemplary multiplexed digital assay performed with two detection channels. The partition contains a copy of a masked target A and a copy of a masking target B. The targets are composed of different sequences, as represented by a thicker template 232 and a thinner template 234 for the targets. The targets are amplified with different pairs of forward and reverse primers ($F_A$ and $R_A$ or $F_B$ and $R_B$). Amplification is reported by different probes ($P_A$ and $P_B$) labeled with distinct fluorophores 148, 242. Fluorescence from each fluorophore is detectable in a different detection channel as a different waveband of emitted light.

Figure 12A:
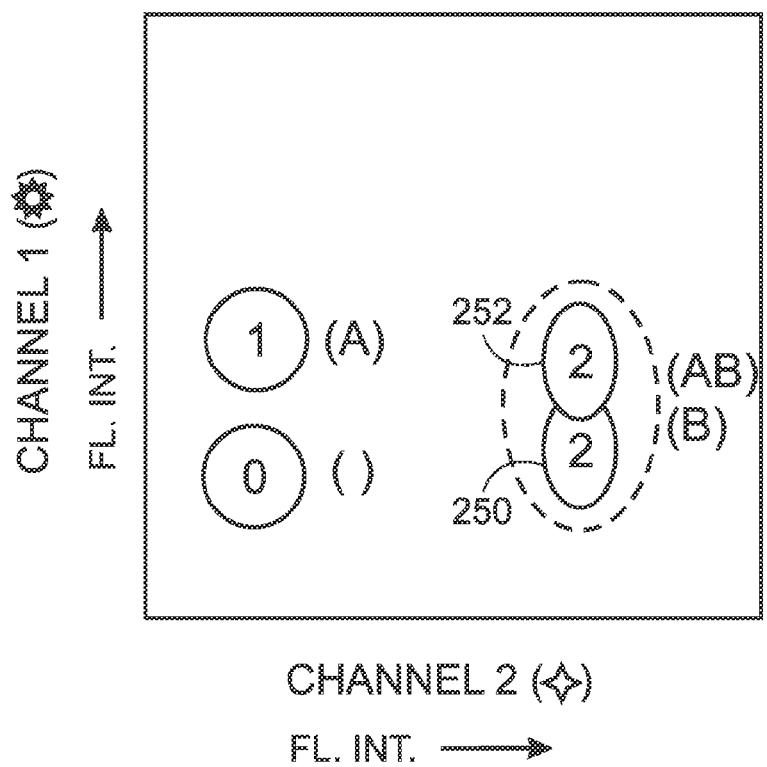
FIG. 12A is a schematic scatter plot of amplification data that may be collected from the multiplexed digital assay of FIG. 12, with three distinct clusters of partitions numbered sequentially and identified according to target content, in accordance with aspects of the present disclosure.

FIG. 12A shows a schematic scatter plot of amplification data collected from the multiplexed assay of FIG. 12. Fluorescence intensity values detected in each channel for each partition are plotted with respect to each channel axis. Fluorophores 148 and 242 are detected substantially exclusively in channels 1 and 2, respectively. Fluorescence intensity data for the partitions create three distinct clusters, which are numbered sequentially (as 0, 1, and 2) and are identified adjacent each cluster according to target content. Cluster "0" represents empty partitions, namely, partitions negative for both targets, indicated as ( ). Cluster "1" represents partitions positive only for target A, indicated as (A). The signal intensity of partitions that are A-positive are relatively close to those that are negative for both targets, but an accurate partition count can be obtained from cluster 1. Cluster "2" represents partitions positive for target B, namely a population 250 of partitions that contain only target B, indicated as (B), and another population 252 of partitions that contain both targets A and B, indicated as (AB). However, populations 250, 252 are not well resolved and thus cannot provide accurate partition counts for (AB) and (B) separately. Accordingly, the concentration of target A can be calculated using only counts $N_0$ and $N_1$ from clusters 0 and 1, respectively, that is, from only a portion of the data that excludes all B-positive partitions (i.e., excluding all counts from cluster 2 ($N_2$)):

$$\lambda_A = \ln(N_0 + N_1) - \ln(N_0) \quad (20)$$

The concentration of target B, on the other hand, can be calculated using all of the partition counts:

$$\lambda_B = \ln(N_0 + N_1 + N_2) - \ln(N_0 + N_1) \quad (21)$$

In other cases, each population of partitions having a particular target content may be resolved from other populations with different target contents. For example, the AB and B populations of FIG. 12A could form a pair of resolved clusters, which would allow calculation of the concentration of each of targets A and B using data from each of the four partition populations/clusters. More particularly, a total count of partitions could be based on partitions from all of the populations/clusters.

IV. MULTIPLEXED ASSAYS WITH A SPECIFIC REPORTER AND A GENERIC REPORTER

This section describes exemplary multiplexed assays for two or more targets performed with at least one specific reporter and a generic reporter; see FIGS. 13-18. The assays shown here are detected in two optical channels. However, detection may be in only one optical channel or three or more optical channels. Any of the multiplexed assays disclosed herein, whether performed only with one or more specific reporters, only with one or more generic reporters, or a combination of specific and generic reporters, may benefit from data exclusion if partition populations with different target content are not resolved from one another in the data.

Intercalating dyes, such as SYBR® Green dye and EvaGreen® dye, are commonly used in PCR to detect production of an amplicon. Assays based on intercalating dyes as reporters are popular as they are less expensive than probe-based assays (e.g., with TaqMan® probes, molecular beacon probes, Scorpion® primers, etc.). However, assays with intercalating dyes are not universally used for at least two reasons. First, these assays are completely reliant on the specificity of the primers to ensure amplification of only the target of interest. For some loci, using only a pair of primers does not provide sufficient specificity, and further specificity is achieved through a labeled probe. The probe increases the specificity of target detection, as unwanted products that are nonspecifically amplified by the primers will not contribute to the detected signal if the probe does not bind to these products. Second, it can be difficult to quantify two targets of a sample in the same well, when using an intercalating dye as the reporter for both targets. However, it is generally desirable to normalize data for a target of interest to at least one reference target (e.g., a housekeeping gene(s)) in the sample.

Without the ability to multiplex in the same well, the sample must be split into multiple wells for separate assays to quantify the target of interest and the reference target. This approach can introduce error, such as pipetting variability between wells. The present disclosure enables multiplexed assays with an intercalating dye as a reporter.

A generic reporter can be used, as described below, in combination with at least one specific reporter (e.g., at least one labeled probe) in a digital assay for accurate single-well quantification. This approach is attractive as it permits investigators to achieve a significant cost savings, while also reducing experimental error, because two or more targets can be quantified simultaneously in a single well.

The multiplexed assays disclosed in this section permit researchers performing gene expression analysis to purchase probe-based assays for their reference genes, and to use primer-based assays with a generic reporter for their genes of interest (GOI). If the researcher is studying many genes, there can be a significant cost savings as only one or a few probes need to be purchased and the other assays can be detected with a generic reporter. Single-well quantification of a target of interest and a reference target can be achieved, thereby eliminating pipetting variability that currently hinders the use of an intercalating dye for gene expression or other studies. In general, measuring more than one target in the same multiplexed assay allows for auto-normalization of the amount of DNA loaded, as used in copy number variation or other applications.

Figure 13:
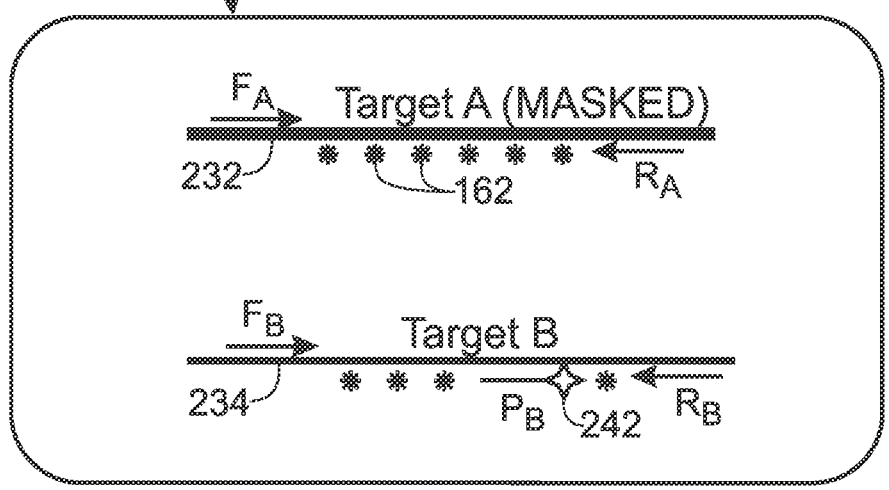
FIG. 13 is a schematic view of a partition from another exemplary multiplexed digital assay performed with two detection channels, with the partition containing a copy of a masked target (A) and a copy of a masking target (B), each amplifiable with a different pair of forward and reverse primers ($F_A$ and $R_A$ or $F_B$ and $R_B$) and detectable via a generic reporter (e.g., an intercalating dye) and a specific probe ($P_B$), in accordance with aspects of the present disclosure.

FIG. 13 shows a partition 260 from another exemplary multiplexed digital assay performed with two detection channels. The multiplexed assay is configured as in FIG. 11, except that the specific reporter for target A is replaced with generic reporter 162, which is capable of binding to the amplicons for both target A and target B. The assay has a specific reporter, probe B ($P_B$), for target B. Target A is masked, at least partially, by the presence of target B. However, the concentrations of both targets can be determined as shown below.

Figure 14:
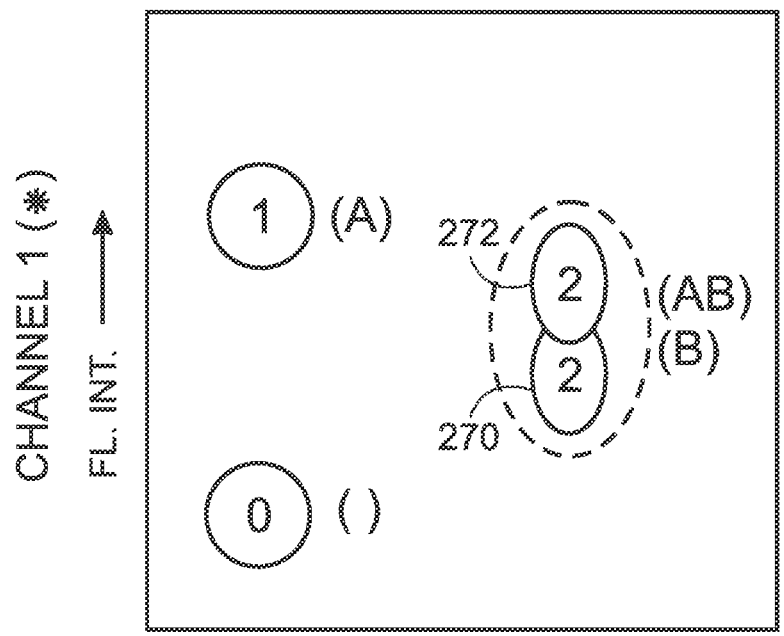
FIG. 14 is a schematic scatter plot of amplification data that may be collected from the multiplexed digital assay of FIG. 13, with three distinct clusters of partitions numbered sequentially and identified according to target content, in accordance with aspects of the present disclosure.

FIG. 14 shows a schematic scatter plot of amplification data that may be collected from the multiplexed digital assay of FIG. 13. Fluorescence intensity values detected in each channel for each partition are plotted with respect to each channel axis. Dye 162, which reports amplification of both targets A and B, and fluorophore 242, which reports amplification of target B only, are detected substantially exclusively in channels 1 and 2, respectively. In other words, there is sufficient spectral separation between the probe-based assay and the intercalating dye to distinguish separate clusters. Fluorescence intensity data for the partitions create three distinct clusters, which are numbered sequentially (as 0, 1, and 2) and are identified adjacent each cluster according to target content as in FIG. 12A. Cluster "2" represents partitions positive for target B, namely a population 270 of partitions that contain only target B, and another population 272 of partitions that contain both targets A and B. However, populations 270, 272 are not well resolved and thus cannot provide accurate partition counts for (AB) and (B) separately. Accordingly, the concentrations of targets A and B can be calculated using Equations 20 and 21, respectively. In an exemplary embodiment, target A is RPP30 and target B is MRG.

In other cases, each population of partitions having a particular target content may be resolved from other populations with different target contents. For example, the AB and B populations of FIG. 14 (or FIG. 14A below) could form a pair of resolved clusters, which would allow calculation of the concentration of each of targets A and B using data from each of the four partition populations/clusters. More particularly, a same total count of partitions used for calculating each concentration could be based on partitions from all of the populations/clusters.

FIG. 14A shows a schematic view of a partition 274 from an exemplary multiplexed digital assay performed with a single detection channel. The multiplexed assay is configured as in FIG. 13, except that probe B ($P_B$) for target B is labeled with fluorophore 148, which allows fluorescence from generic reporter 162 and fluorophore 148 of probe B to be detected in the same channel. Partition 274 contains a copy of target A and target B, each amplifiable with a different pair of forward and reverse primers ($F_A$ and $R_A$ or $F_B$ and $R_B$).

FIG. 14B shows a schematic graph of fluorescence intensity data collected from five sets of partitions (lanes 1-5) in a single detection channel for the multiplexed digital assay of FIG. 14A. Partition sets 1-5 contain the same concentrations of targets A and B and of both pairs of primers, but have a variable concentration of the probe ($P_B$) specific for target B.

Lane 1 represents signal detected from generic reporter 162 only (probe B is not present). Partition populations containing target A only (A), target B only (B), or both targets A and B (AB) have an increased signal amplitude and are well separated from the negative partitions ( ). However, the three target-positive populations are not resolved from each other.

Lanes 2-5 represent signal detected from the assay performed with an increasing concentration of probe B. The position of the band for target A may not change, but each of the B-positive bands migrates upward in the graph with increased concentrations of probe B, to produce a clear separation of the B-negative and B-positive populations. Accordingly, the data of lane 4 or lane 5 can be utilized to accurately determine the concentrations of targets A and B. The concentration of target A can be determined from only a subset of the data, namely, from partition counts of the negative band ( ) and the A-only band (A), with Equation 20. The concentration of target B can be determined from partition counts of all of the bands in either lane, with Equation 21.

Figure 15:
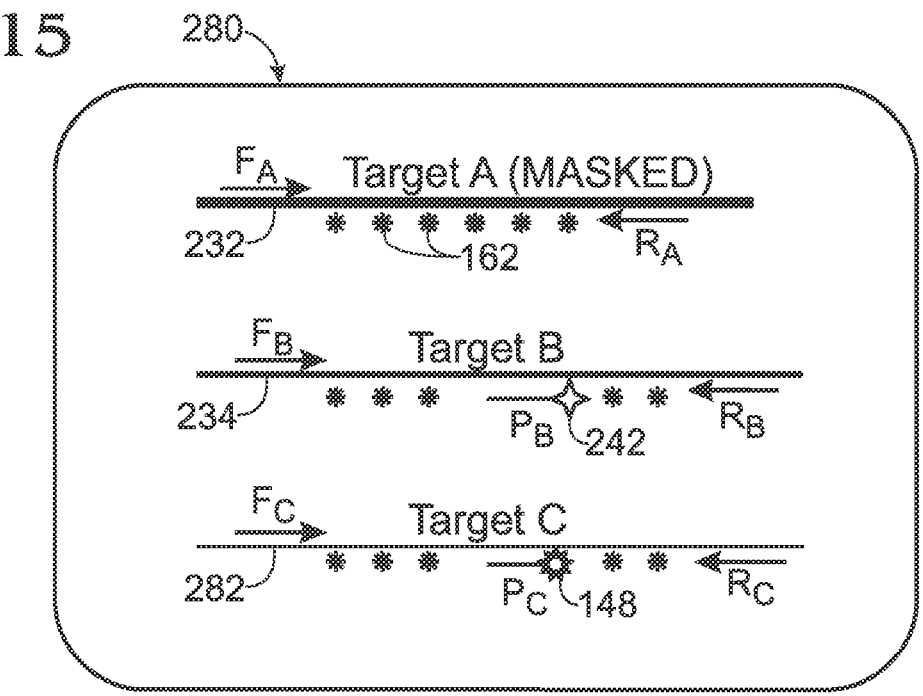
FIG. 15 is a schematic view of a partition from another exemplary multiplexed digital assay performed with two detection channels, with the partition containing a copy of a masked target (A), a second target (B), and a masking target (C), each amplifiable with a different pair of forward and reverse primers ($F_A$ and $R_A$, $F_B$ and $R_B$, or $F_C$ and $R_C$) and detectable via a generic reporter (e.g., an intercalating dye) and specific probes ($P_B$ and $P_C$), in accordance with aspects of the present disclosure.

FIG. 15 is a schematic view of a partition 280 from an exemplary multiplexed digital assay performed with two detection channels and three unlinked targets (A-C). The multiplexed assay configuration of FIG. 15 is related to that of FIG. 13, except that an assay for another, unrelated target (C) is performed (a copy of a template 282 for the target is present in partition 280). Target C is amplified with target C-specific primers ($F_C$ and $R_C$), and amplification is reported by a target C-specific probe ($P_C$), which is labeled with fluorophore 148. The exact number and arrangement of clusters will depend on various parameters, such as the condition(s) limiting each amplification reaction, the channels used for detection, the effective concentration of each reporter, the spectral characteristics of each reporter, and the like. Any suitable combination of the parameters can be adjusted to achieve a cluster arrangement that permits accurate concentration determination.

Figure 16:
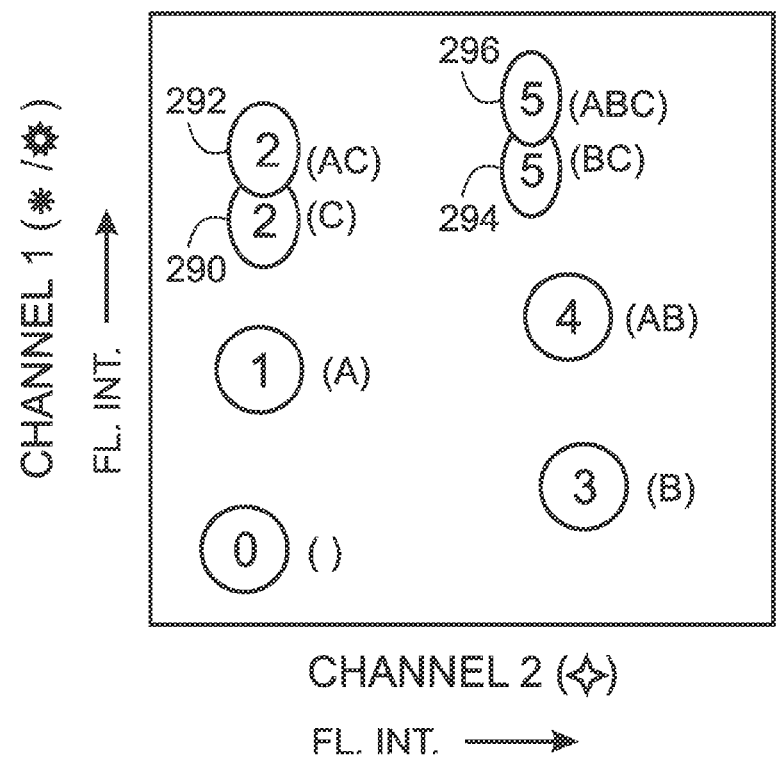
FIG. 16 is a schematic scatter plot of amplification data that may be collected from the multiplexed digital assay of FIG. 15 in a first channel that detects amplification of targets A and C and in a second channel that detects amplification of target B, with five distinct clusters of target-positive partitions numbered sequentially and identified according to target content, in accordance with aspects of the present disclosure.

FIG. 16 is a schematic scatter plot of amplification data collected from the multiplexed digital assay of FIG. 15. Fluorescence intensity (FL. INT.) values detected in each channel for each partition are plotted with respect to each channel axis. Dye 162 and fluorophore 148 (target C) are detected substantially exclusively in channel 1, and fluorophore 242 (target B) is detected substantially exclusively in channel 2. Fluorescence intensity data for the partitions create six distinct clusters, which are numbered sequentially (as 0, 1, 2, 3, 4, and 5) and are identified adjacent each cluster in parentheses according to target content. Cluster 2 represents partitions positive for target C, namely a population 290 of partitions that contain only target C, and another population 292 of partitions that contain both targets A and C. Cluster 5 represents partitions positive for targets B and C, namely, a population 294 of partitions that contain only target B and C, and another population 296 of partitions that contain all three targets. However, populations 290, 292 and populations 294, 296 are not well resolved and thus cannot provide accurate partition counts for each individual population. However the concentrations of targets A, B, and C can be calculated with proper combination and exclusion of cluster counts.

The concentration of target A can be calculated as follows:

$$\lambda_A = \ln(N_0 + N_1) - \ln(N_0) \tag{22}$$

Alternatively, the concentration of target A can be calculated by including clusters 3 and 4 and excluding all C-positive clusters:

$$\lambda_A = \ln(N_0 + N_1 + N_3 + N_4) - \ln(N_0 + N_3) \tag{23}$$

The concentration of target B can be calculated using counts from all the partitions as follows:

$$\lambda_B = \ln(N_{tot}) - \ln(N_0 + N_1 + N_2) \tag{24}$$

Alternatively, the concentration of target B can be calculated by excluding counts from all C-positive clusters (i.e., by excluding $N_2$ and $N_5$):

$$\lambda_B = \ln(N_0 + N_1 + N_3 + N_4) - \ln(N_0 + N_1) \tag{25}$$

Clusters 2 and 5 can be excluded from the calculation because each is expected to have the same fraction of A-positive partitions as all of the partitions considered collectively. However, generally, it is desirable to use more of the data for a calculation, if accuracy does not suffer.

The concentration of target C can be calculated by excluding all B-positive clusters (i.e., by excluding $N_3$, $N_4$, and $N_5$):

$$\lambda_C = \ln(N_0 + N_1 + N_2) - \ln(N_0 + N_1) \tag{26}$$

Alternatively, the concentration of target C can be calculated using counts from all the partitions as follows:

$$\lambda_C = \ln(N_{tot}) - \ln(N_0 + N_1 + N_3 + N_4) \tag{27}$$

Figure 17:
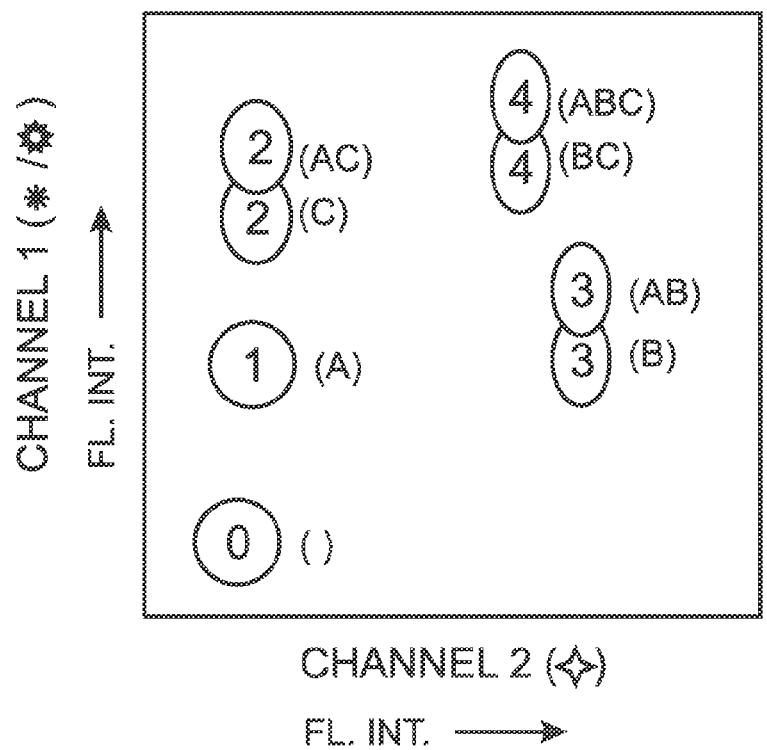
FIG. 17 is another schematic scatter plot of amplification data that may be collected from the multiplexed digital assay of FIG. 15 and plotted as in FIG. 16, except that two of the clusters ((A) and (AB)) of FIG. 16 are no longer resolved and form a heterogeneous cluster with heterogeneous target content.

FIG. 17 shows another schematic scatter plot of amplification data collected from the multiplexed digital assay of FIG. 15 and plotted as in FIG. 16, except that cluster 3 (B) and cluster 4 (AB) have merged to form a new cluster 3, and cluster 5 has been renamed as cluster 4.

Here, again, the concentrations of all targets can be calculated. The concentration of target A can be calculated with Equation 22. The concentration of target B can be calculated using counts from all of the partitions with Equation 24. Alternatively, the concentration of target B can be calculated by excluding counts from all C-positive clusters (i.e., by excluding $N_2$ and $N_4$):

$$\lambda_B = \ln(N_0 + N_1 + N_3) - \ln(N_0 + N_1) \tag{28}$$

The concentration of target C can be calculated by excluding all B-positive clusters (i.e., by excluding $N_3$ and $N_4$) using Equation 26. Alternatively, the concentration of target C can be calculated using counts from all the partitions as follows:

$$\lambda_C = \ln(N_{tot}) - \ln(N_0 + N_1 + N_3) \tag{29}$$

Figure 18:
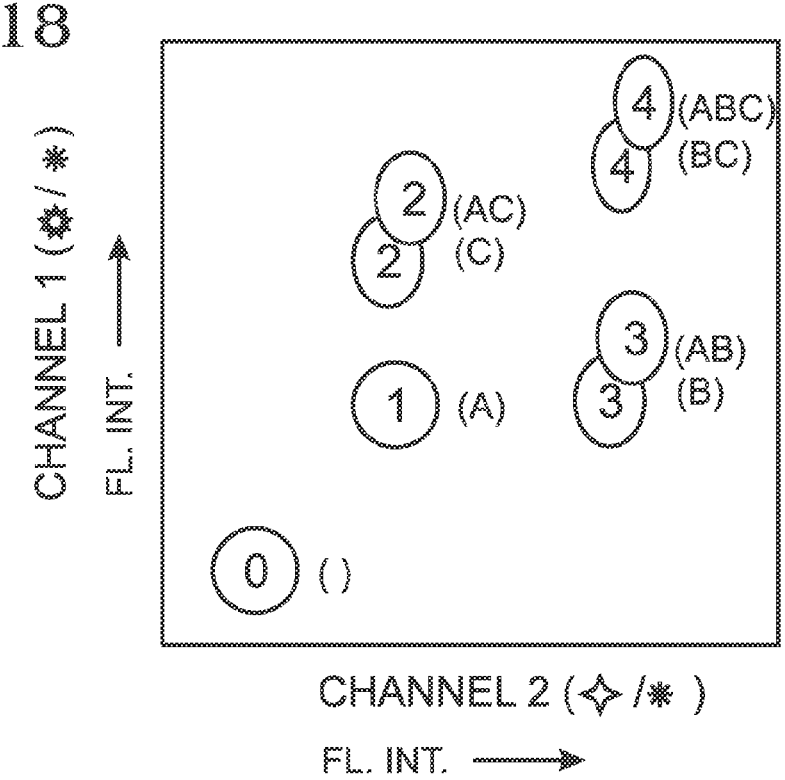
FIG. 18 is another schematic scatter plot of amplification data that may be collected from the multiplexed digital assay of FIG. 15, but with a first channel that detects amplification of targets A and C and a second channel that detection amplification of targets A and B, with four distinct clusters of target-positive partitions numbered sequentially and identified according to target content, in accordance with aspects of the present disclosure.

FIG. 18 shows yet another schematic scatter plot of amplification data collected from the multiplexed digital assay of FIG. 15. Fluorescence intensity (FL. INT.) values detected in each channel for each partition are plotted with respect to each channel axis. Generic reporter 162 is detected in both channels 1 and 2, fluorophore 148 (target C) substantially exclusively in channel 1, and fluorophore 242 (target B) substantially exclusively in channel 2. Fluorescence intensity data for the partitions create five distinct clusters, which are numbered sequentially (as 0, 1, 2, 3, and 4) and are identified adjacent each cluster in parentheses according to target content. The clusters of FIG. 18 correspond to those of FIG. 17; the strategies of FIG. 17 for calculating concentration of targets A-C can be applied to the cluster counts of FIG. 18.

V. EXAMPLES

This section describes selected aspects and embodiments of the present disclosure related to multiplexed digital assays. The assays may involve any combination of target masking, data exclusion for calculation of at least one target level, use of the same generic reporter for at least two targets in the same multiplexed assay, and/or use of a specific reporter and a generic reporter for the same multiplexed assay, among others. These examples are intended for illustration only and should not limit or define the entire scope of the present disclosure.

Example 1

Analysis of Library Quality

Figure 19:
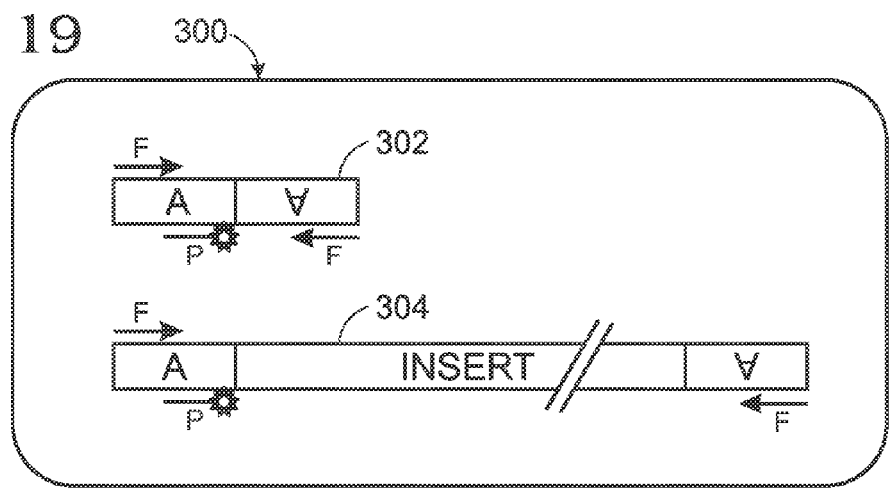
FIG. 19 is a schematic view of a partition from an exemplary multiplexed digital assay to determine the quality of a library, with the partition containing a copy of an empty library member (an adapter-adapter inverted repeat with no insert) and a copy of a library member containing an insert, with each library member being amplifiable with two copies of the same primer (F) and detectable with an adapter-specific probe (P), in accordance with aspects of the present disclosure.
Figure 20:
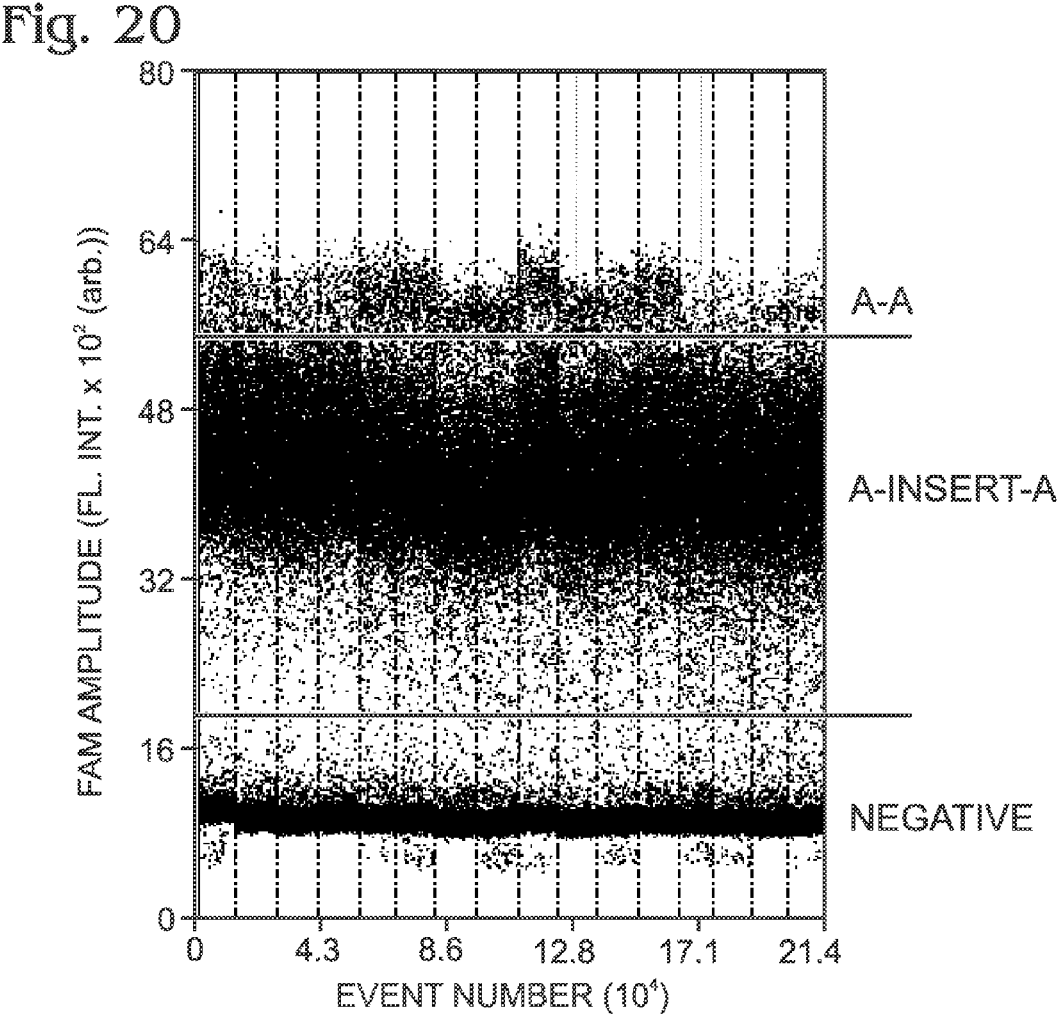
FIG. 20 is a graph of amplification data collected from the multiplexed assay of FIG. 19 performed in droplets.

This example describes use of a multiplexed digital assay in droplets to measure levels of empty and filled members of a library, where the presence of an empty library member in a droplet masks the presence of a filled member in the same droplet; see FIGS. 19 and 20.

FIG. 19 shows a schematic view of a partition 300 from an exemplary multiplexed digital assay to determine the quality of a library, such as an Ion Torrent® library. The library may be a Next-Generation Sequencing (NGS) library constructed in vitro by attaching a copy of an adapter ("A") to each end of a population of fragments of interest. Members of the library can include an empty member 302 produced by ligation of a pair of adapter copies to each other in an inverted orientation, without an intervening insert. Empty members 302 do not provide useful sequence information and thus are an undesired component of the library. The goal of library construction is to generate a high-complexity population of filled members, such as member 304, each containing one of the fragments of interest as an insert flanked by attached copies of the adapter.

The quality of an NGS library can be characterized in a multiplexed digital assay. Members of the library can be distributed at partial occupancy to partitions, such as droplets. The droplets can contain one or more primers (F) to amplify members of the library and an adapter-specific probe (P) to report amplification. Here, the same primer (F) can function as a forward primer and a reverse primer for amplification by binding specifically to both copies of the adapter.

FIG. 20 shows a graph of amplification data collected from the multiplexed assay of FIG. 19 performed in droplets. The probe is labeled with FAM dye. Fluorescence intensity measured from the FAM dye is plotted as a function of event (or droplet) number. The empty library member (A-A), which is very short, amplifies very efficiently and produces a stronger signal than a filled library member, which masks the signal from the filled library member, if present in the same droplet. Accordingly, the concentrations of empty and filled library members can be calculated as described for FIG. 3. In particular, the concentration of empty library members, which are dominant/masking, can be calculated using counts from all the droplets, and the concentration of the filled library members, which are masked, can be calculated by excluding the counts for the empty library members. Exemplary concentrations obtained with this approach are shown below for four libraries:

| Library | Total Concentration | A-A Concentration |
|---|---|---|
| N13 | 574 | 19.7 |
| N14 | 539 | 30.0 |
| N15 | 631 | 29.8 |
| N16 | 581 | 9.17 |

Further aspects of library construction and characterization by digital assay are described in U.S. patent application Ser. No. 13/562,198, filed Jul. 30, 2012, which is incorporated herein by reference.

Example 2

Measurement of Spliced and Unspliced RNA Levels

This example describes use of a multiplexed digital assay in droplets to measure levels of unspliced and spliced transcripts in a sample; see FIGS. 21-24.

Figure 21:
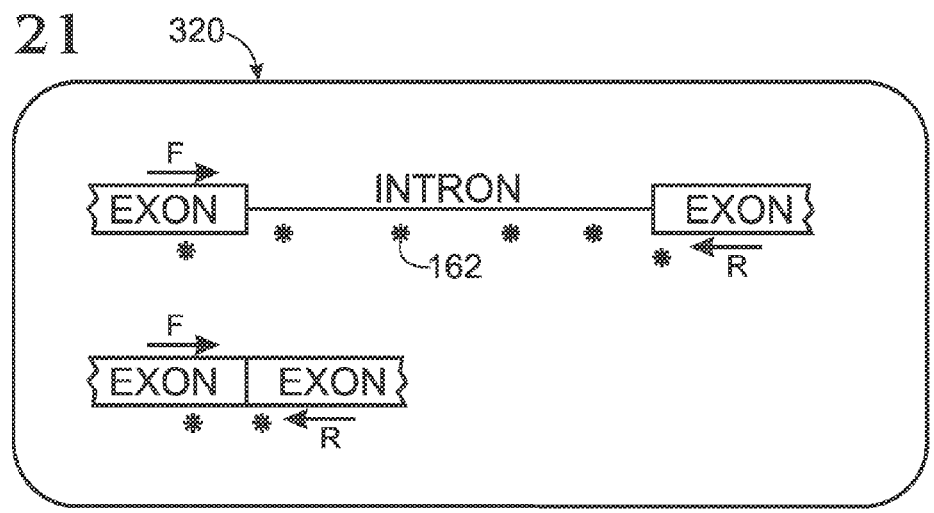
FIG. 21 is a schematic view of a partition from an exemplary multiplexed digital assay to quantify spliced and unspliced species in a sample, with the partition containing a copy of an unspliced species (Exon-Intron-Exon) and a spliced species (Exon-Exon), with each species being amplifiable with the same pair of forward and reverse primers (F and R) and detectable via a generic reporter, in accordance with aspects of the present disclosure.

FIG. 21 shows a schematic view of a partition 320 from an exemplary multiplexed digital assay to quantify spliced and unspliced species in a sample. Partition 320 contains a copy of an unspliced species (Exon-Intron-Exon) and a spliced species (Exon-Exon). Each species is amplifiable with the same pair of forward and reverse primers (F and R). Amplification is reported via light emission from dye 162, which binds nonspecifically to amplicons generated by amplification of target from both templates.

Figure 22:
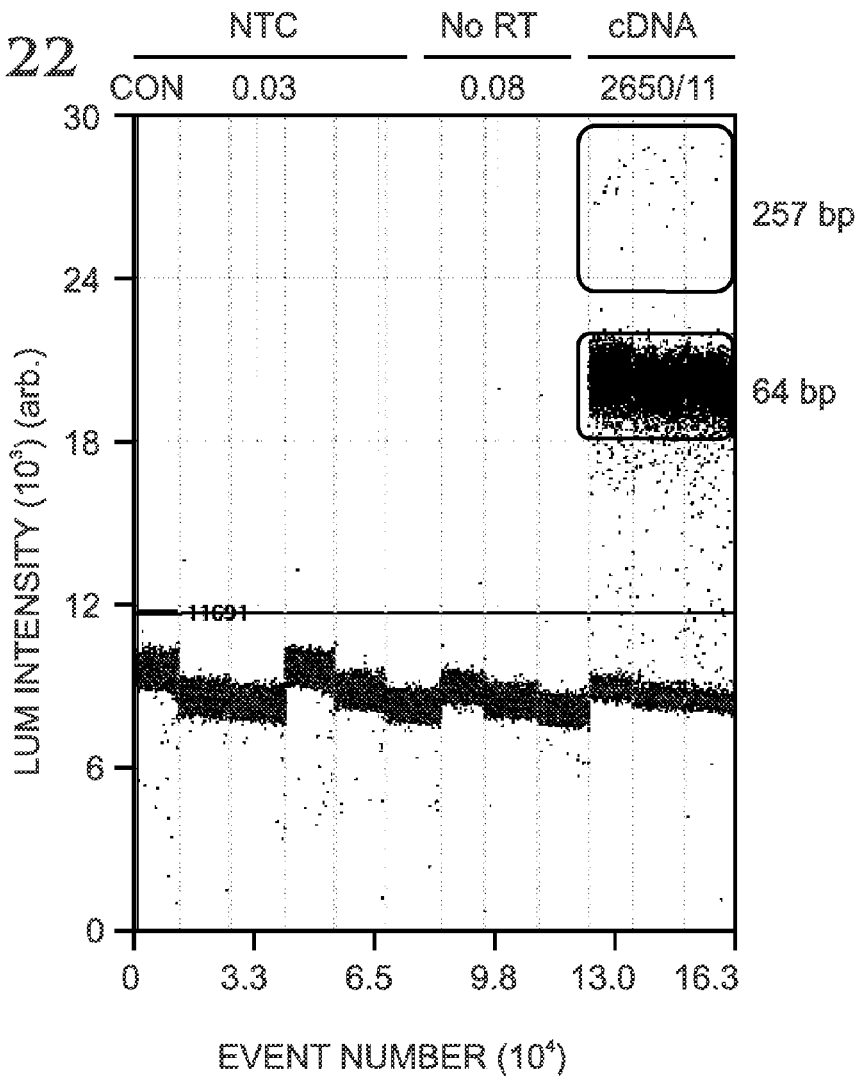
FIG. 22 is a graph of amplification data collected from the multiplexed assay of FIG. 21 performed in droplets.

FIG. 22 shows a graph of amplification data collected from the multiplexed assay of FIG. 21 performed in droplets with primers to exons 7 and 8 of GAPDH, and SBYR® Green as dye 162. The expected amplicon sized is 64 bp for the spliced species with the intron removed. Additional droplets with higher intensity signals are visible with an amplicon size of 257 bp, which may be produced from immature mRNA molecules where the introns have not yet been excised. The 64 bp species outcompetes the 257 bp species and masks its signal. Note the inversion of signal since the dye is intercalating and produces signal proportional to amplicon length (also see FIGS. 4 and 7). The concentration calculated for the 257 bp species was confirmed in an assay using intron primers to amplify the intron, without competition from the shorter, spliced species.

Figure 23:
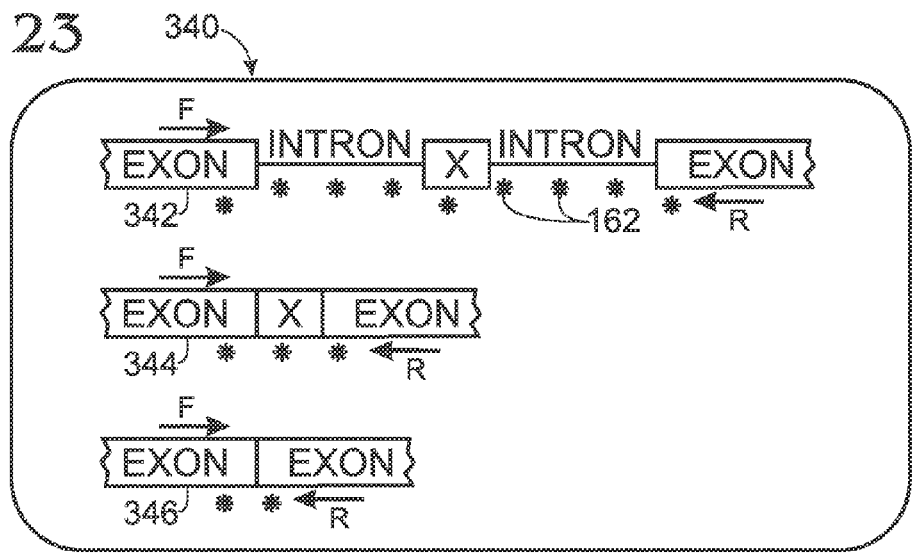
FIG. 23 is a schematic view of a partition from another exemplary multiplexed digital assay to quantify spliced and unspliced species in a sample, with the partition containing a copy of an unspliced species (Exon-Intron-X-Intron-Exon) and two distinct spliced species (Exon-X-Exon and Exon-Exon), with each species being amplifiable with the same pair of forward and reverse primers (F and R) and detectable via a generic reporter, in accordance with aspects of the present disclosure.

FIG. 23 shows a partition 340 from another exemplary multiplexed digital assay to quantify spliced and unspliced species in a sample. The partition contains a copy of an unspliced species 342 (Exon-Intron-X-Intron-Exon) and two distinct spliced species 344, 346 (Exon-X-Exon and Exon-Exon). Each species is amplifiable with the same pair of forward and reverse primers (F and R). Amplification of each species is reported by the same dye 162.

Figure 24:
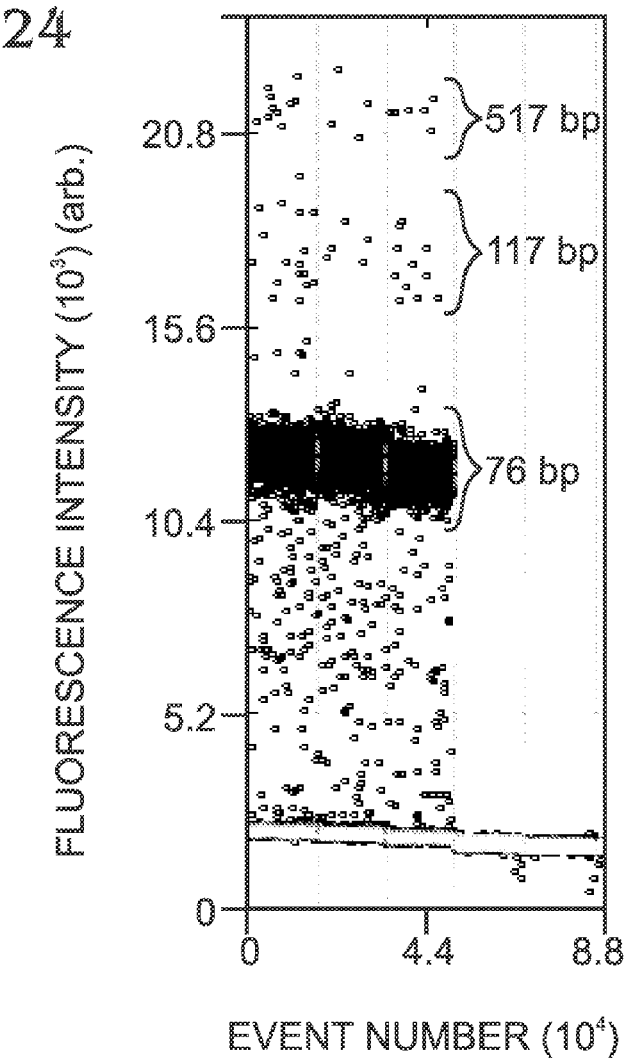
FIG. 24 is a graph of amplification data collected from the multiplexed assay of FIG. 23.

FIG. 24 shows a graph of amplification data collected from the multiplexed assay of FIG. 23 performed in droplets with primers to exons 3 and 4 of actin. Here, three amplicons of different length (76 bp, 117 bp, and 517 bp) are visible. The shortest amplicon outcompetes both longer amplicons, and the intermediate amplicon outcompetes the longest amplicon. Concentrations of the three targets can be computed as described in Section II.

Further aspects of multiplexed assays for insertions and deletions are described in U.S. Provisional Patent Application Ser. No. 61/692,635, filed Aug. 23, 2012, which is incorporated herein by reference.

Example 3

Multiplexed Digital Assay with a Reporter-Less Target

Figure 25:
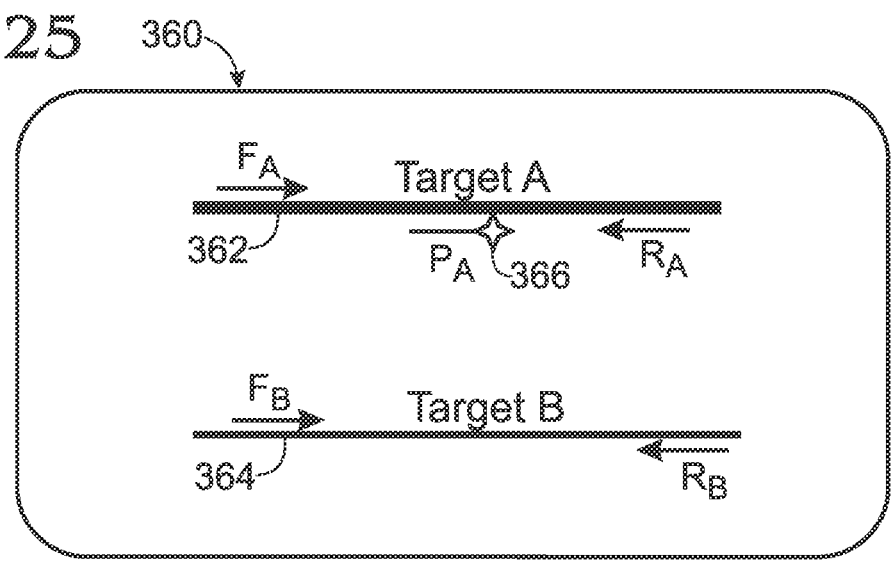
FIG. 25 is a schematic view of a partition from an exemplary multiplexed digital assay to quantify a pair of targets (targets A and B) in partitions, with the depicted partition containing a copy of each target and only a single reporter that binds to only one of the targets (target A), in accordance with aspects of the present disclosure.
Figure 26:
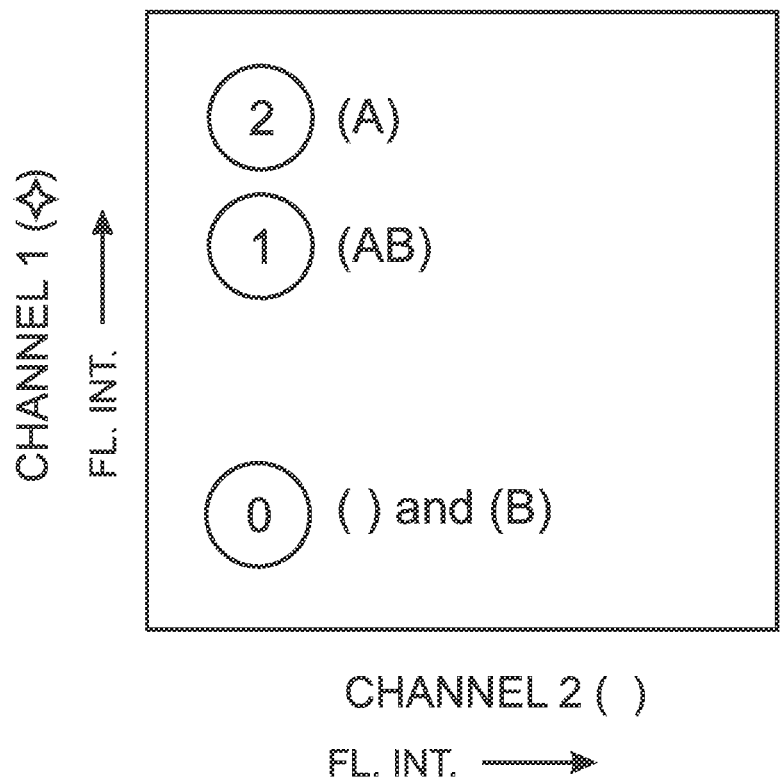
FIG. 26 is a schematic plot of amplification data that may be collected from the multiplexed digital assay of FIG. 25 in a pair of optical channels, with only one of the channels detecting the single reporter, and with the plot having three distinct clusters of partitions numbered sequentially (0, 1, and 2) and identified according to target content, in accordance with aspects of the present disclosure.

This example describes a multiplexed digital assay performed in partitions to measure levels of a pair of targets, and using a single reporter that binds to only one of the targets; see FIGS. 25 and 26.

FIG. 25 shows an exemplary partition 360 from an exemplary multiplexed digital assay for a first target (target A) and a second target (target B). Partition 360 may be a member of a set of partitions having copies of target A and target B randomly distributed among the partitions. Only a subset of the partitions each contain at least one copy of target A. Only a different subset of the partitions each contain at least one copy of target B. Yet another different subset of the partitions each contain at least one copy of target A and at least one copy of target B, with partition 360 shown in FIG. 25 as an example.

Each partition may include or be an isolated portion of a mixture. The mixture may contain targets A and B (e.g., provided by templates 362 and 364, respectively), and also may contain reagents sufficient to amplify each target under appropriate environmental conditions or manipulation (e.g., heating, cyclical heating and cooling, or the like).

Any suitable reagents may be included in the mixture and thus in each partition 360. The reagents may include forward and reverse primers ($F_A$ and $R_A$) for amplification of target A, and forward and reverse primers ($F_B$ and $R_B$) for amplification of target B. The reagents also may include a specific reporter (e.g., a probe, $P_A$, including a label, photoluminophore 366). The reporter binds specifically to target A (and/or to a region of an amplicon formed by amplification of target A). However, the mixture does not contain a reporter that binds to target B or that is sensitive to amplification of target B, except indirectly. More particularly, the presence of target B is detectable via probe $P_A$, as a change in the probe signal, only when both targets A and B are amplified in the same partition, such as in partition 360 that contains a copy of each target. Without the presence of target A in a partition, target B remains invisible and undetectable for the partition.

FIG. 26 shows a schematic scatter plot of amplification data (fluorescence intensity) that may be collected from partitions in the multiplexed digital assay of FIG. 25. The plot shows data collected in two channels, but photoluminophore 366 of probe A is detectable only in channel 1. In other cases, the data may be plotted as intensity with respect to time or event number. In any event, three clusters of partitions are distinguishable and are numbered sequentially (0, 1, and 2) and are identified adjacent each cluster according to target content.

Cluster 0 has the lowest intensity in channel 1, because each partition of cluster 0 is negative for target A. Since target A is absent, amplification of unprobed target B goes undetected. Therefore, target B is distributed among the partitions of cluster 0 at about the same average concentration (copy per droplet) as for the partitions in all of the clusters, considered collectively. Any given partition of cluster 0 can be positive or negative for target B.

Cluster 2 has the highest intensity in channel 1 and contains target A only. Amplification of target A occurred in the partitions of cluster 2 without competition from target B, which results in more efficient amplification of target A and thus a stronger signal from the probe.

Cluster 1 has an intermediate intensity in channel 1. Each partition of cluster 1 amplifies target A and target B. The A and B amplification reactions compete with one another for limiting reagents, which results in less efficient amplification of target A relative to the partitions of cluster 2. As a result, the probe produces a signal of lesser intensity for cluster 1 than for cluster 2.

$N_0$, $N_1$, and $N_2$ are the number of partitions (the partition counts) in clusters 0, 1, and 2, respectively. The concentration (copies per droplets) of target A then can be calculated as follows:

$$\lambda_A = \ln(N_0+N_1+N_2) - \ln(N_0) \tag{30}$$

In Equation 30, the total number of partitions is provided by summing the partition numbers for all three clusters, and the number of partitions negative for target A only by the number of partitions in cluster 0 (also see Equation 5 above).

The concentration (copies per droplets) of target B can be calculated as follows:

$$\lambda_B = \ln(N_1+N_2) - \ln(N_2) \tag{31}$$

In Equation 31, the total number of partitions may be determined by summing the partition numbers for clusters 1 and 2, and the number of partitions negative for target B by the number of partitions in cluster 2 (also see Equation 5 above). Cluster 0 can be excluded from the calculation of the target B concentration because the concentration of target B in cluster 0 is expected to be the same (absent statistical error) as in clusters 1 and 2, taken collectively.

Example 4

Selected Embodiments I

This example describes selected embodiments of multiplexed digital assays performed with a generic reporter, presented as a series of numbered paragraphs.

1. A method of performing a multiplexed digital assay, the method comprising: (A) providing partitions containing a first target and a second target at partial occupancy; (B) amplifying the targets in the partitions; (C) collecting data for amplification of the first target and the second target in the partitions from one or more reporters including a generic reporter that binds to amplicons representing both targets; and (D) determining a concentration of the first target and the second target based on the data.

2. The method of paragraph 1, wherein a plurality of the partitions each contain a copy of both targets.

3. The method of paragraph 1 or 2, wherein the concentration of the first target is determined from only a subset of the data that selectively excludes partitions positive for the second target.

4. The method of any of paragraphs 1 to 3, wherein at least one same primer is used for amplification of both targets.

5. The method of paragraph 4, wherein amplification of each target is performed with a same pair of primers.

6. The method of any of paragraphs 1 to 3, wherein amplification of each target is performed with a pair of primers, only one of which or neither of which binds to the other target.

7. The method of any of paragraphs 1 to 6, wherein the generic reporter includes a dye that binds to double-stranded nucleic acid.

8. The method of paragraph 7, wherein multiple copies of the dye bind to double-stranded nucleic acid in direct relation to a length of the nucleic acid.

9. The method of paragraph 7 or 8, wherein the dye is an intercalating dye.

10. The method of any of paragraphs 7 to 9, wherein the dye becomes more luminescent when bound to the double-stranded nucleic acid.

11. The method of any of paragraphs 1 to 10, wherein the partitions are droplets.

12. The method of any of paragraphs 1 to 11, wherein the one or more reporters include a probe that binds to the second target and not the first target.

13. The method of paragraph 12, wherein the data includes a signal created by detecting light emitted by the probe.

14. The method of any of paragraphs 1 to 13, wherein the concentration of the first target is determined from only a first subset of the data, and wherein the concentration of the second target is determined from only a distinct second subset of the data or with all of the data.

15. The method of any of paragraphs 1 to 14, wherein the one or more reporters include a probe for a third target, and wherein the data includes data for amplification of the third target in the partitions.

16. The method of paragraph 15, wherein the step of collecting data includes a step of detecting, in the same optical channel, light emitted from the generic reporter and from the probe.

17. The method of paragraph 1, wherein all of the data represents light emitted by the generic reporter.

18. The method of paragraph 1, wherein amplification of the first target is detected only as light emitted by a generic reporter.

19. A method of performing a multiplexed digital assay, the method comprising: (A) providing partitions containing a first target and a second target at partial occupancy, each partition containing a generic reporter that binds to amplicons representing both targets, with a plurality of the partitions each containing a copy of both targets; (B) amplifying the targets in the partitions; (C) collecting data from the generic reporter for amplification of the first target and the second target in the partitions; and (D) determining a concentration of the first target from only a subset of the data that selectively excludes partitions positive for the second target.

20. A method of performing a multiplexed digital assay, the method comprising: (A) providing partitions containing a first target and a second target at partial occupancy, each partition containing a generic reporter that binds to amplicons representing both targets and a probe that binds specifically to an amplicon representing the second target, with a plurality of the partitions each containing a copy of both targets; (B) amplifying the targets in the partitions; (C) collecting data for amplification of the first target and the second target in the partitions, at least in part by detecting light emitted by the generic reporter and the probe; and (D) determining a concentration of the first target from only a subset of the data that selectively excludes partitions positive for the second target.

21. The method of paragraph 20, wherein the step of collecting data includes collecting data for amplification of a third target in the partitions, further comprising a step of determining a concentration of the second target and the third target.

22. The method of paragraph 21, wherein the subset of the data also selectively excludes partitions positive for the third target.

23. The method of paragraph 21 or 22, wherein the subset of the data includes partitions positive for the third target.

24. The method of any of paragraphs 21 to 23, wherein each partition includes a probe that binds specifically to an amplicon representing the third target.

25. The method of paragraph 24, where the probe that binds specifically to an amplicon representing the third target does not bind to an amplicon representing the first target and does not bind to an amplicon representing the second target.

26. The method of any of paragraphs 21 to 25, wherein the step of collecting data is performed in first and second optical channels representing different wavebands of light, wherein amplification of the third target is detectable in the first optical channel, and wherein amplification of the second target is detectable in the second channel.

27. The method of any of paragraphs 20 to 26, wherein the probe includes a luminophore, wherein the step of collecting data is performed in first and second optical channels representing different wavebands of emitted light, wherein light emitted by the generic reporter is detected at least substantially exclusively in the first optical channel, and wherein light emitted by the luminophore is detected at least substantially exclusively in the second optical channel.

28. The method of any of paragraphs 20 to 27, wherein the generic reporter includes an intercalating dye.

29. The method of any of paragraphs 20 to 26 or 28, wherein the probe includes a luminophore, and wherein the step of collecting data includes detecting light emitted in the same waveband by the generic reporter and the probe.

Example 5

Selected Embodiments II

This example describes selected embodiments of multiplexed digital assays each performed with a specific reporter and a generic reporter, presented as a series of numbered paragraphs.

1. A method of performing a multiplexed digital assay, the method comprising: (A) providing partitions each including a portion of a same mixture, the mixture containing a first target and a second target and also containing a generic reporter that is sensitive to amplification of either target and a specific reporter that is specifically sensitive to amplification of the second target, wherein only a first subset of the partitions each contain at least one copy of the first target and only a distinct second subset of the partitions each contain at least one copy of the second target; (B) amplifying the first target and the second target in the partitions; (C) collecting amplification data from the generic reporter and the specific reporter present in a plurality of the partitions; and (D) calculating a level of each target based on the amplification data.

2. A method of performing a multiplexed digital assay, the method comprising: (A) providing partitions each including a portion of a same mixture, the mixture containing a first target and a second target and also containing a generic reporter and a specific reporter, wherein only a subset of the partitions each contain at least one copy of the first target and only another subset of the partitions each contain at least one copy of the second target; (B) amplifying the targets in the partitions to generate a first amplicon corresponding to the first target and a second amplicon corresponding to the second target, wherein the generic reporter binds to the first amplicon and the second amplicon, and wherein the specific reporter binds to the second amplicon and not the first amplicon; (C) collecting amplification data from a plurality of the partitions by detecting light emitted by the generic reporter and at least one luminophore of the specific reporter; and (D) calculating a level of each target based on the amplification data.

3. The method of paragraph 1 or 2, wherein each partition of a distinct third subset of the partitions contains at least one copy of both targets.

4. The method of paragraph 3, wherein partitions of the third subset are not reliably distinguishable from partitions of the first subset or the second subset in the amplification data.

5. The method of paragraph 3 or 4, wherein the partitions of the third subset contribute to the level calculated for at least one of the targets.

6. The method of any of paragraphs 3 to 5, wherein calculation of a level of at least one of the targets is performed with only a portion of the amplification data that selectively excludes partitions of the third subset.

7. The method of any of paragraphs 1 to 6, wherein all of the data is collected from the plurality of partitions at about a same temperature.

8. The method of any of paragraphs 1 to 7, wherein the level is a concentration.

9. The method of any of paragraphs 1 to 8, further comprising a step of determining a copy number variation of one of the targets based on the level of each target.

10. The method of paragraph 9, wherein the partitions provided contain nucleic acid from a genome, wherein one of the first and second targets is a reference target having a known copy number in the genome and the other of the first and second targets is a target of interest having an unknown copy number in the genome.

11. The method of any of paragraphs 1 to 10, wherein the mixture includes primers for amplification of each target.

12. The method of any of paragraphs 1 to 11, wherein the mixture contains a complete set of reagents to support amplification of each target.

13. The method of any of paragraphs 1 to 12, wherein the specific reporter has an intact form and one or more degraded forms, wherein the one or more degraded forms are produced from the intact form during amplification of the second target, and wherein the step of collecting amplification data includes collection of data from the one or more degraded forms of the specific reporter.

14. The method of any of paragraphs 1 to 13, wherein the step of collecting amplification data is performed in at least a first optical channel and a second optical channel, and wherein the first optical channel detects light that is spectrally distinct from light detected in the second optical channel.

15. The method of paragraph 14, wherein light emitted by the generic reporter is detected at least predominantly only in the first optical channel relative to the second optical channel, and wherein light emitted by the at least one luminophore of the specific reporter is detected at least predominantly only in the second optical channel relative to the first optical channel.

16. The method of paragraph 14, wherein light emitted by the generic reporter is detected in each of the first optical channel and the second optical channel, and wherein light emitted by the at least one luminophore of the specific reporter is detected at least predominantly only in the second optical channel relative to the first optical channel.

17. The method of any of paragraphs 1 to 16, wherein the second amplicon includes a pair of complementary strands, and wherein the specific reporter binds to a region of only one of the complementary strands.

18. The method of any of paragraphs 1 to 17, wherein the level of the one of the targets is calculated from only a subset of the amplification data that selectively excludes partitions testing positive for the other of the targets.

19. The method of any of paragraphs 1 to 18, wherein the partitions are droplets.

20. The method of any of paragraphs 1 to 19, wherein the generic reporter includes an intercalating dye.

21. The method of any of paragraphs 1 to 20, wherein the amplification data is collected after an endpoint of amplification has been reached for each of the targets.

22. The method of any of paragraphs 1 to 21, wherein the step of calculating a level includes a step of plotting the amplification data to generate a scatter plot having a first axis and a second axis, wherein each axis represents a range of intensities of light detected in a different optical channel, and wherein the scatter plot includes at least two clusters of data points with each cluster representing partitions positive for at least one of the targets.

23. The method of paragraph 22, wherein the step of calculating a level of each target includes a step of calculating a level of at least one of the targets using only a subset of the data that excludes at least one of the clusters.

24. The method of any of paragraphs 1 to 23, wherein the first target and the second target are not covalently linked to each other in a majority of the partitions.

25. The method of paragraph 24, wherein the first target and the second target are not covalently linked to each other in the partitions.

26. The method of any of paragraphs 1 to 25, wherein all of the data is collected from partitions at a temperature that is below a melting temperature of each of the amplicons.

27. The method of any of paragraphs 1 to 26, wherein the data is collected from a plurality of partitions while copies of the first amplicon and copies of the second amplicon in at least a subset of the plurality of partitions remain in at least partially double-stranded form.

28. The method of any of paragraphs 1 to 27, wherein all of the data is collected with at least a portion of the first amplicon and at least a portion of the second amplicon in double-stranded form.

29. The method of any of paragraphs 1 to 28, wherein all of the data is collected from partitions at a temperature below about 50 degrees Celsius.

30. The method of any of paragraphs 1 to 29, wherein the specific reporter includes a nucleic acid that binds specifically to the second amplicon.

31. The method of any of paragraphs 1 to 30, further comprising a step of classifying individual partitions as positive or classifying individual partitions as negative for at least one of the targets based on the amplification data.

32. The method of paragraph 31, further comprising a step of determining a number of partitions classified as positive or classified as negative for one of the targets, and wherein the step of calculating a level for the one target is based on the number of partitions classified as positive or classified as negative.

33. A composition for performing a multiplexed digital assay, comprising: (A) a plurality of droplets disposed in a same continuous phase, the droplets each including a portion of a same mixture, wherein the mixture contains a first target, a second target, a generic reporter that is sensitive to amplification of either target, and a specific reporter that is specifically sensitive to amplification of the second target, wherein only a first subset of the plurality of droplets each contain at least one copy of the first target and only a distinct second subset of the plurality of droplets each contain at least one copy of the second target, and wherein the mixture includes a complete set of reagents for amplification of each target.

34. The composition of paragraph 33, wherein the continuous phase includes oil.

35. The composition of paragraph 34, wherein the oil includes a fluorocarbon oil, a silicone oil, or both.

36. The composition of paragraph 33, wherein the continuous phase is a liquid at room temperature.

37. The composition of paragraph 36, wherein the continuous phase is a liquid at 90 degrees Celsius.

38. The composition of paragraph 33, wherein a third subset of the droplets each contain at least one copy of each target.

39. The composition of paragraph 33, wherein the complete set of reagents includes dNTPs, primers for amplifying each target, and a heat-stable polymerase.

Example 6

Selected Embodiments III

This example describes selected embodiments of multiplexed digital assays, presented as a series of numbered paragraphs.

1. A method of performing a multiplexed digital assay, the method comprising: (A) providing partitions containing a first target and a second target at partial occupancy, with a plurality of the partitions each containing a copy of both targets; (B) performing a reaction corresponding to each target in the partitions; (C) collecting data from at least one reporter for each reaction; and (D) determining a concentration of the first target from only a subset of the data that selectively excludes partitions positive for the second target.

2. The method of paragraph 1, wherein the partitions are droplets, wherein the step of collecting data is performed by a detection assembly, wherein the step of determining is performed with a data processor, or any combination thereof.

3. The method of paragraph 2, wherein the step of providing partitions includes a step of forming droplets containing the first target and the second target.

4. The method of any of paragraphs 1 to 3, wherein the step of providing partitions includes a step of forming partitions including a sample containing the first target and the second target.

5. The method of any of paragraphs 1 to 4, wherein the first target and the second target each include a sequence of nucleotides.

6. The method of any of paragraphs 1 to 5, wherein a plurality of the partitions each contain a single copy of the first target and a plurality of the partitions each contain a single copy of the second target when the partitions are provided.

7. The method of any of paragraphs 1 to 6, wherein the reaction corresponding to each target amplifies nucleic acid.

8. The method of any of paragraphs 1 to 7, wherein the reaction corresponding to each target is catalyzed by at least one enzyme.

9. The method of paragraph 8, wherein the at least one enzyme includes a polymerase, a ligase, or both.

10. The method of paragraph 8, wherein the at least one enzyme includes an enzyme connected to an oligonucleotide that binds specifically to one of the targets.

11. The method of any of paragraphs 1 to 10, wherein the at least one reporter for each reaction includes a reporter that binds to nucleic acid.

12. The method of paragraph 11, wherein a reporter for at least one of the reactions is a labeled probe that includes an oligonucleotide.

13. The method of paragraph 12, wherein the step of performing a reaction produces a first amplicon corresponding to the first target and a second amplicon corresponding to the second target, wherein a reporter for the reaction corresponding to the first target binds to the first amplicon and the second amplicon.

14. The method of paragraph 13, wherein a reporter for the reaction corresponding to the second target is a specific reporter that binds specifically to the second amplicon relative to the first amplicon, or wherein the data is collected from only one reporter.

15. A method of performing a multiplexed digital assay, the method comprising: (A) amplifying a first target and a second target in partitions containing each target at partial occupancy; (B) collecting data for amplification of the first target and the second target, the second target at least partially masking the presence of the first target in the data for a plurality of the partitions that contain a copy of each target; and (C) determining a concentration of the first target from only a subset of the data that selectively excludes partitions positive for the second target.

16. The method of paragraph 15, wherein the partitions are droplets.

17. The method of paragraph 15 or 16, wherein each of the targets is present in the partitions at an average of less than five copies per partition.

18. The method of any of paragraphs 15 to 17, wherein each of a plurality of the partitions contains no copy of either target.

19. The method of any of paragraphs 15 to 18, wherein the concentration is an average number of copies per partition of the first target.

20. The method of any of paragraphs 15 to 19, wherein the step of determining is based on a value for a total number of partitions represented by the subset of the data.

21. The method of any of paragraphs 15 to 20, wherein the step of determining is based on a value representing a total number of partitions in the subset of the data that are negative for the first target, or on a value representing a total number of partitions in the subset of the data that are positive for the first target.

22. The method of any of paragraphs 15 to 21, wherein the step of determining is based on Poisson statistics.

23. The method of any of paragraphs 15 to 22, further comprising a step of determining a concentration of the second target based on at least a subset of the data.

24. The method of paragraph 23, wherein the steps of amplifying and collecting are performed for a third target, and wherein the concentration of the second target is determined from only a subset of the data that excludes partitions positive for the third target.

25. The method of any of paragraphs 15 to 24, wherein amplification of the second target suppresses amplification of the first target in partitions containing a copy of each target.

26. The method of any of paragraphs 15 to 25, wherein at least one same primer is used for amplification of the first target and the second target.

27. The method of paragraph 26, wherein a same pair of forward and reverse primers is used for amplification of the first target and the second target.

28. The method of paragraph 26 or 27, wherein amplification of the first target and the second target generates respective first and second amplicons, and wherein the first amplicon is substantially longer than the second amplicon, or vice versa.

29. The method of paragraph 28, wherein the second amplicon is at least 25%, 50%, or 100% longer than the first amplicon, or vice versa.

30. The method of any of paragraphs 15 to 29, further comprising a step of identifying from the data at least one cluster of partitions positive for the second target, wherein the step of determining is performed with the at least one cluster excluded.

31. The method of paragraph 30, further comprising a step of generating at least one plot of the data, wherein the step of identifying is performed based on the least one plot.

32. The method of any of paragraphs 15 to 31, further comprising a step of identifying the subset of the data based on comparing one or more signal values for each partition with one or threshold values or ranges.

33. The method of paragraph 32, wherein the one or more signal values represent a detected intensity of emitted light.

34. The method of any of paragraphs 15 to 33, wherein amplification of the first target and second target generates respective first and second amplicons, and wherein the each of the partitions contains a same reporter that binds to the first amplicon and the second amplicon.

35. The method of paragraph 34, wherein the same reporter is a dye that binds to double-stranded nucleic acid.

36. The method of paragraph 34 or 35, wherein the same reporter binds to the first and second amplicons without substantial sequence specificity.

37. The method of paragraph 34, wherein the same reporter is a probe that binds specifically to the first and second amplicons.

38. The method of any of paragraphs 15 to 37, wherein the step of amplifying also amplifies a third target, wherein the data collected is also for amplification of the third target in the partitions, wherein the third target at least partially masks the presence of the second target for partitions that contain a copy of each of the second and third targets, further comprising a step of determining a concentration of the second target from only a subset of the data that selectively excludes partitions positive for the third target.

39. The method of paragraph 38, wherein the third target at least partially masks the presence of the first target in the data for partitions that contain a copy of each of the first and third targets.

40. The method of paragraph 38 or 39, wherein the step of determining a concentration of the first target is performed with only a subset of the data that selectively excludes partitions positive for the second target and selectively excludes partitions positive for the third target.

41. The method of any of paragraphs 15 to 40, wherein the subset of the data from which the concentration of the first target is determined excludes at least a majority of the partitions positive for the second target.

42. The method of paragraph 41, wherein the subset of the data excludes all partitions that test positive for the second target.

43. A method of performing a multiplexed digital assay, the method comprising: (A) providing partitions containing a first target and a second target at partial occupancy, with a plurality of the partitions each containing a copy of both targets; (B) amplifying the targets in the partitions; (C) collecting data for amplification of the first target and the second target, the data being plottable to produce three or more clusters of data points with each cluster representing at least one different combination of the targets in the partitions; and (D) determining a concentration of the first target from only a subset of the data that excludes one or more of the clusters.

44. The method of paragraph 43, wherein one of the three or more clusters represents partitions that are negative for both targets.

45. The method of paragraph 43 or 44, wherein one of the three or more clusters represents partitions that are positive for the first target and negative for the second target.

46. The method of any of paragraphs 43 to 45, wherein one of the three or more clusters represents partitions that are positive for the second target without regard to whether the partitions are positive or negative for the first target.

47. The method of any of paragraphs 43 to 46, further comprising a step of plotting the data to form the clusters.

48. The method of paragraph 47, wherein the data is plotted as luminescence intensity as a function of event number.

49. The method of paragraph 47, wherein the data is plotted to generate a two-dimensional scatter plot having a first axis and a second axis, and wherein each axis represents intensity for a different waveband of light.

50. The method of any of paragraphs 43 to 49, wherein one of the three or more clusters includes a pair of sub-clusters representing different combinations of the targets, and wherein the sub-clusters overlap one another.

Example 7

Selected Embodiments IV

This example describes selected embodiments of multiplexed digital assays, presented as a series of numbered paragraphs.

1. A method of performing a multiplexed digital assay, the method comprising: (A) providing a mixture including a plurality of targets and reagents sufficient for amplification of each of the targets, wherein the plurality of targets includes a first target; (B) forming partitions each including a portion of the mixture; (C) amplifying the plurality of targets in the partitions; (D) collecting data from a plurality of the partitions for amplification of each of the plurality of targets; (E) identifying partition populations in the data, each partition population having a different target content of the plurality of targets; and (F) calculating a level of the first target from only a portion of the data, wherein the portion of the data is collected from only a subset of the plurality of the partitions, wherein the subset of partitions excludes two or more of the partition populations, and wherein the two or more excluded partition populations include at least a pair of excluded partition populations that are not resolved from each other in the data.

2. The method of paragraph 1, wherein the at least a pair of excluded partition populations that are not resolved from each other include a first partition population that is positive for the first target and a second partition population that is negative for the first target.

3. The method of paragraph 1 or 2, wherein the step of identifying partition populations includes a step of plotting the data to form three or more clusters of data points, wherein each cluster represents at least one of the partition populations, wherein the portion of the data excludes one or more of the clusters, and wherein the one or more excluded clusters include a heterogeneous cluster composed of at least two overlapping sets of data points representing partition populations having different target content from one another.

4. The method of paragraph 3, wherein each data point represents one or more intensity values of light detected from each partition of the plurality of the partitions, and wherein the step of plotting the data includes a step of plotting the data with respect to at least one intensity axis.

5. The method of paragraph 4, where the step of plotting the data includes a step of plotting the data with respect to at least two intensity axes.

6. The method of any of paragraphs 1 to 5, wherein the step of collecting data includes a step of obtaining at least one value for each partition of the plurality of the partitions, and wherein the step of identifying is based on comparing the at least one signal value to at least one threshold or range for each partition of the plurality of the partitions.

7. The method of any of paragraphs 1 to 6, wherein the plurality of targets includes a second target, and wherein the portion of the data excludes each partition testing positive for the second target.

8. The method of paragraph 7, wherein the step of amplifying is performed with a same pair of primers for the first target and the second target.

9. The method of paragraph 7 or 8, wherein a subset of the plurality of the partitions each contain at least one copy of the first target and at least one copy of the second target, and wherein amplification of the second target reduces amplification of the first target in partitions each containing a copy of the first target and the second target.

10. The method of any of paragraphs 7 to 9, wherein the plurality of targets includes a third target, further comprising a step of calculating a level of the second target based on only a portion of the data that excludes partitions testing positive for the third target.

11. The method of any of paragraphs 1 to 10, wherein the level is an average number of copies per partition of the first target in the subset of partitions, and wherein the average number is expected to be the same, absent statistical error, as an average number of copies per partition of the first target in the two or more excluded partition populations taken collectively.

12. The method of any of paragraphs 1 to 11, wherein the step of identifying partition populations includes a step of identifying a partition population that tests negative for each of the plurality of targets.

13. The method of paragraph 12, wherein the subset of partitions does not include the partition population that tests negative for each of the plurality of targets.

14. The method of any of paragraphs 1 to 13, wherein the step of identifying partition populations includes a step of identifying at least a pair of the partition populations that are not resolved from each other in a plot of the data.

15. The method of paragraph 14, wherein the subset of partitions does not include the at least a pair of partition populations that are not resolved from each other in a plot of the data.

16. The method of any of paragraphs 1 to 15, wherein only a first subset of the plurality of the partitions each contain at least one copy of the first target, wherein only a distinct second subset of the plurality of the partitions each contain at least one copy of a second target of the plurality of targets, and wherein a third subset of the plurality of the partitions each contain at least one copy of the first target and the second target.

17. The method of any of paragraphs 1 to 16, further comprising a step of obtaining a first partition count and a second partition count from the subset of partitions, wherein the step of calculating a level is performed with the first partition count and the second partition count.

18. The method of paragraph 17, wherein the first partition count is a total number of partitions in the subset of partitions, and wherein the second partition count is a number of partitions positive for the first target in the subset of partitions or a number of partitions negative for the first target in the subset of partitions.

19. The method of any of paragraphs 1 to 18, wherein the step of forming partitions includes a step of forming droplets.

20. The method of any of paragraphs 1 to 19, wherein each target of the plurality of targets includes a sequence of nucleotides.

21. The method of any of paragraphs 1 to 20, wherein the mixture includes at least one reporter, and wherein the step of collecting data includes a step of detecting light from the at least one reporter.

22. The method of paragraph 21, wherein the at least one reporter includes a same reporter that is sensitive to amplification of the first target and a second target of the plurality of targets.

23. The method of paragraph 22, wherein the same reporter is a generic reporter.

24. The method of paragraph 23, wherein the generic reporter binds to double-stranded nucleic acid without substantial sequence specificity.

25. The method of any of paragraphs 21 to 24, wherein the at least one reporter includes a labeled probe that bind specifically to only the first target of the plurality of targets.

26. The method of any of paragraphs 1 to 25, wherein the step of calculating a level includes a step of calculating a concentration of the first target.

27. The method of paragraph 26, wherein the step of calculating a concentration of the first target includes a step of calculating an average number of copies of the first target per partition.

28. The method of any of paragraphs 1 to 27, wherein the step of calculating a level is based on Poisson statistics.

29. The method of any of paragraphs 1 to 28, wherein the step of amplifying the first target generates an amplicon, and wherein the partitions do not include a reporter that binds to the first target, the amplicon, or both the first target and the amplicon.

30. The method of any of paragraphs 1 to 29, wherein the plurality of targets include a second target, and wherein the partitions include a reporter that is differentially sensitive to amplification of the second target in a partition relative to amplification of the first target and the second target in the partition.

31. A method of performing a multiplexed digital assay, the method comprising: (A) providing a mixture including a plurality of targets and reagents sufficient for amplification of each of the targets, wherein the plurality of targets includes a first target and a second target; (B) forming partitions each including a portion of the mixture; (C) amplifying the plurality of targets in the partitions; (D) collecting data from a plurality of the partitions for amplification of each of the plurality of targets, the data being plottable to form three or more clusters of data points, with each data point representing a partition, and with each cluster having a different content of the plurality of targets; and (E) calculating a level of the first target from only a portion of the data that excludes at least one of the clusters of data points, wherein the at least one excluded cluster includes a heterogeneous excluded cluster composed of overlapping sets of data points representing at least two excluded partition populations, wherein at least one of the excluded partition populations is positive for the first target, and wherein at least one of the excluded partition populations is negative for the first target.

32. The method of paragraph 31, further comprising a step of plotting the data to form the three or more clusters of data points.

33. The method of paragraph 31 or 32, further comprising a step of identifying each cluster according to the target content of the cluster.

34. The method of paragraph 33, wherein the portion of the data excludes at least a pair of heterogeneous clusters.

35. The method of any of paragraphs 31 to 34, wherein the plurality of targets includes a second target, and wherein the portion of the data excludes data points for partitions testing positive for the second target.

36. The method of any of paragraphs 31 to 35, wherein the portion of the data excludes data points for partitions testing negative for each of the plurality of targets.

37. A method of performing a multiplexed digital assay, the method comprising: (A) providing a mixture including a first target, a second target, and reagents sufficient for amplification of each of the targets; (B) forming partitions each including a portion of the mixture; (C) amplifying the first target and the second target in the partitions; (D) collecting data from a plurality of the partitions for amplification of the first target and the second target; and (E) calculating a level of the first target from only a portion of the data that excludes each partition testing positive for the second target.

38. The method of paragraph 37, wherein first target is not linked to the second target in the mixture and is not linked to the second target when the step of forming partitions is performed.

39. The method of paragraph 37 or 38, wherein the data is collected from at least one reporter including a labeled probe.

40. The method of paragraph 39, wherein the labeled probe has an intact form and one or more degraded forms, and wherein the step of collecting data includes a step of collecting at least part of the data from one or more degraded forms of the probe.

41. The method of any of paragraphs 37 to 40, wherein a presence of the second target at least partially masks a presence of the first target in the data for a plurality of the partitions each containing at least one copy of each target.

42. The method of any of paragraphs 37 to 41, wherein the portion of the data is collected from only a subset of the plurality of the partitions, wherein the step of calculating a level is based on a total number partitions in the subset of the partitions and on a number of partitions in the subset of the partitions that are negative for the first target or that are positive for the first target.

43. A method of performing a multiplexed digital assay, the method comprising: (A) amplifying a first target and a second target in partitions containing each target at partial occupancy; (B) collecting data for amplification of the first target and the second target, the second target at least partially masking a presence of the first target in the data for a plurality of the partitions that each contain at least one copy of each target; and (C) calculating a concentration of the first target from only a portion of the data that selectively excludes partitions testing positive for the second target.

44. The method of paragraph 43, wherein the step of calculating is based on a value for a total number of partitions represented by the portion of the data.

45. The method of paragraph 44, wherein the step of calculating is based on a value for a number of partitions in the portion of the data that test negative for the first target, or on a value for a number of partitions in the portion of the data that test positive for the first target.

46. The method of any of paragraphs 43 to 45, further comprising a step of calculating a level of the second target based on at least a portion of the data.

47. The method of any of paragraphs 43 to 46, wherein the steps of amplifying and collecting data are performed for a third target, further comprising a step of calculating a level of the second target from only a portion of the data that excludes partitions testing positive for the third target.

48. The method of any of paragraphs 43 to 47, wherein amplification of the second target reduces amplification of the first target in partitions each containing a copy of each target.

49. The method of any of paragraphs 43 to 48, further comprising a step of identifying from the data at least one cluster of partitions positive for the second target, wherein the step of calculating is performed with the at least one cluster excluded.

50. A method of performing a multiplexed digital assay, the method comprising: (A) providing a mixture including a plurality of targets and reagents sufficient for amplification of each of the targets, wherein the plurality of targets includes a first target and a second target; (B) forming partitions each including a portion of the mixture, with only a first subset of the partitions containing the first target and only a distinct second subset of the partitions containing the second target, and with a distinct third subset of the partitions each containing at least one copy of each of the first target and the second target; (C) amplifying the plurality of targets in the partitions; (D) collecting data from a plurality of the partitions for amplification of each of the plurality of targets, the data being plottable to produce three or more clusters of data points with each cluster representing at least one target combination not represented by any other of the three or more clusters; and (E) calculating a level of the first target from only a portion of the data that excludes one or more of the clusters, wherein the one or more excluded clusters include an excluded cluster that is heterogeneous with respect to the first target (i.e., only a subset the cluster is positive for the first target).

51. The method of paragraph 50, wherein the at least one target combination includes a combination in which each of the plurality of targets is absent.

52. The method of paragraph 50 or 51, wherein the at least one target combination includes a combination in which only one target of the plurality of targets is present.

53. The method of any of paragraphs 50 to 52, wherein the at least one target combination includes a combination in which the first target is absent and the second target is present.

54. The method of any of paragraphs 50 to 53, wherein every cluster containing the second target is excluded from the step of calculating a level.

55. The method of any of paragraphs 50 to 54, wherein the level is a concentration, wherein the concentration is an average number of copies per partition, and wherein the average number is expected to be the same, absent statistical error, as an average number of copies per partition of the first target in the one or more excluded clusters taken collectively.

56. The method of any of paragraphs 50 to 55, wherein the step of calculating a level uses a value for a total number of partitions represented by the portion of data, and wherein partitions of the one or more clusters are not included in the total number of partitions.

57. The method of any of paragraphs 50 to 56, wherein one of the three or more clusters includes data points for partitions that are negative for the first target and the second target.

58. The method of any of paragraphs 50 to 57, wherein one of the three or more clusters includes data points for partitions that are positive for the first target and negative for the second target.

59. The method of any of paragraphs 50 to 58, wherein the excluded cluster that is heterogeneous with respect to the first target includes data points for partitions that are positive for the first target and data points for partitions that are negative for the first target.

60. The method of any of paragraphs 50 to 59, further comprising a step of plotting the data to form the clusters.

61. The method of paragraph 60, wherein the data is plotted as photoluminescence intensity as a function of event number.

62. The method of paragraph 60, wherein the data is plotted to generate a two-dimensional scatter plot having a first axis and a second axis, and wherein each axis represents detected intensity for a different wavelength or waveband of light.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of performing a multiplexed digital assay, the method comprising:
   providing partitions each including a portion of a same mixture, the mixture containing a first target and a second target and also containing a generic reporter that is sensitive to amplification of either target and a specific reporter that is specifically sensitive to amplification of the second target, wherein only a first subset of the partitions each contain at least one copy of the first target and only a distinct second subset of the partitions each contain at least one copy of the second target;
   amplifying the first target and the second target in the partitions;
   collecting amplification data from the generic reporter and the specific reporter present in a plurality of the partitions; and
   calculating a level of each target based on the amplification data.

2. The method of claim 1, wherein each partition of a distinct third subset of the partitions contains at least one copy of both targets.

3. The method of claim 2, wherein the partitions of the third subset contribute to the level calculated for at least one of the targets.

4. The method of claim 3, wherein partitions of the third subset are not reliably distinguishable from partitions of the first subset or the second subset in the amplification data.

5. The method of claim 1, wherein the level is a concentration.

6. The method of claim 1, further comprising a step of determining a copy number of one of the targets based on the level of each target.

7. The method of claim 1, wherein the mixture contains a complete set of reagents to support amplification of each target.

8. The method of claim 1, wherein the specific reporter has an intact form and one or more degraded forms, wherein the one or more degraded forms are produced from the intact form during amplification of the second target, and wherein the step of collecting amplification data includes collection of data from the one or more degraded forms of the specific reporter.

9. A method of performing a multiplexed digital assay, the method comprising:
   providing partitions each including a portion of a same mixture, the mixture containing a first target and a second target and also containing a generic reporter and a specific reporter, wherein only a subset of the partitions each contain at least one copy of the first target and only another subset of the partitions each contain at least one copy of the second target;
   amplifying the targets in the partitions to generate a first amplicon corresponding to the first target and a second amplicon corresponding to the second target, wherein the generic reporter binds to the first amplicon and the second amplicon, and wherein the specific reporter binds to the second amplicon and not the first amplicon;
   collecting amplification data from a plurality of the partitions by detecting light emitted by the generic reporter and at least one luminophore of the specific reporter; and
   calculating a level of each target based on the amplification data.

10. The method of claim 9, wherein the step of collecting amplification data is performed in at least a first optical channel and a second optical channel, and wherein the first optical channel detects light that is spectrally distinct from light detected in the second optical channel.

11. The method of claim 10, wherein light emitted by the generic reporter is detected at least predominantly only in the first optical channel relative to the second optical channel, and wherein light emitted by the at least one luminophore of the specific reporter is detected at least predominantly only in the second optical channel relative to the first optical channel.

12. The method of claim 10, wherein light emitted by the generic reporter is detected in each of the first optical channel and the second optical channel, and wherein light emitted by the at least one luminophore of the specific reporter is detected at least predominantly only in the second optical channel relative to the first optical channel.

13. The method of claim 9, wherein the second amplicon includes a pair of complementary strands, and wherein the specific reporter binds to a region of only one of the complementary strands.

14. The method of claim 9, wherein the level of the one of the targets is calculated from only a subset of the amplification data that selectively excludes partitions testing positive for the other of the targets.

15. The method of claim 9, wherein the partitions are droplets.

16. The method of claim 9, wherein the amplification data is collected after an endpoint of amplification has been reached for each of the targets.

17. The method of claim 9, wherein the step of calculating a level includes a step of plotting the amplification data to generate a scatter plot having a first axis and a second axis, wherein each axis represents a range of intensities of light detected in a different optical channel, and wherein the scatter plot includes at least two clusters of data points with each cluster representing partitions positive for at least one of the targets.

18. The method of claim 17, wherein the step of calculating a level of each target includes a step of calculating a level of at least one of the targets using only a subset of the data that excludes at least one of the clusters.

19. The method of claim 1, wherein the level of one of the targets is calculated from only a portion of the amplification data that selectively excludes partitions testing positive for the other target.

20. The method of claim 19, wherein the step of calculating a level includes a step of plotting the amplification data to generate a scatter plot having a first axis and a second axis, wherein each axis represents a range of intensities of light detected in a different optical channel, and wherein the scatter plot includes at least two clusters of data points with each cluster representing partitions positive for at least one of the targets.

* * * * *